(12) United States Patent
Kim et al.

(10) Patent No.: US 7,622,584 B2
(45) Date of Patent: Nov. 24, 2009

(54) IMIDAZOPYRIDINE-BASED COMPOUND AND ORGANIC LIGHT EMITTING DIODE INCLUDING ORGANIC LAYER COMPRISING THE IMIDAZOPYRIDINE-BASED COMPOUND

(75) Inventors: Hee-Yeon Kim, Suwon-si (KR);
Seung-Gak Yang, Suwon-si (KR);
Jung-Han Shin, Suwon-si (KR);
Chang-Ho Lee, Suwon-si (KR);
Hee-Joo Ko, Suwon-si (KR)

(73) Assignee: Samsung Mobile Display Co., Ltd., Yongin (KR)

( * ) Notice: Subject to any disclaimer, the term of this patent is extended or adjusted under 35 U.S.C. 154(b) by 198 days.

(21) Appl. No.: 11/923,555

(22) Filed: Oct. 24, 2007

(65) Prior Publication Data
US 2008/0125593 A1    May 29, 2008

(30) Foreign Application Priority Data
Nov. 24, 2006  (KR) .................. 10-2006-0117092
Jul. 24, 2007   (KR) .................. 10-2007-0074097

(51) Int. Cl.
*C07D 491/02* (2006.01)
*C07D 498/02* (2006.01)
(52) U.S. Cl. .................................... 546/121
(58) Field of Classification Search .................. 546/121
See application file for complete search history.

(56) References Cited

U.S. PATENT DOCUMENTS 4,356,429 A    10/1982   Tang 6,559,256 B2    5/2003   Holmes et al.
2006/0154105 A1 *  7/2006  Yamamoto et al. .......... 428/690

FOREIGN PATENT DOCUMENTS

| EP | 1 582 516 A1 | 10/2005 |
| EP | 1 651 012 A1 | 4/2006 |
| JP | 11-329734 | 11/1999 |
| KR | 10-2005-0078472 | 8/2005 |

OTHER PUBLICATIONS

Patent Abstracts of Japan, Publication No. 11-329734; Date of Publication: Nov. 30, 1999; in the name of Yoshiharu Sato, et al.
Korean Patent Abstracts, Publication No. 1020050078472A; Date of Publication: Aug. 5, 2005; in the name of Seok Jong Lee et al.
European Search Report dated Mar. 4, 2008, for European Application No. 01720635.3, indicating relevance of references listed in this Information Disclosure Statement.
Korean Office action dated Nov. 14, 2008, for corresponding Korean application 10-2007-0074097, noting references listed in an IDS filed May 6, 2008.

* cited by examiner

*Primary Examiner*—D. Margaret Seaman
*Assistant Examiner*—Niloofar Rahmani
(74) *Attorney, Agent, or Firm*—Christie, Parker & Hale, LLP

(57) ABSTRACT

Imidazopyridine-based compounds and organic light emitting diodes (OLEDs) including organic layers including the imidazopyridine-based compounds are provided. The organic light emitting diodes including organic layers having the imidazopyridine-based compounds have low driving voltages, high efficiencies, high luminance, long life-times and low power consumption.

13 Claims, 3 Drawing Sheets

IMIDAZOPYRIDINE-BASED COMPOUND AND ORGANIC LIGHT EMITTING DIODE INCLUDING ORGANIC LAYER COMPRISING THE IMIDAZOPYRIDINE-BASED COMPOUND

CROSS-REFERENCE TO RELATED PATENT APPLICATION

This application claims priority to and the benefit of Korean Patent Application Nos. 10-2006-0117092 and 10-2007-0074097, filed on Nov. 24, 2006 and Jul. 24, 2007, respectively, in the Korean Intellectual Property Office, the entire content of which is incorporated herein by reference.

BACKGROUND OF THE INVENTION

1. Field of the Invention

The present invention relates to imidazopyridine-based compounds and to organic light emitting diodes including organic layers comprising the imidazopyridine-based compounds. More particularly, the invention is directed to imidazopyridine-based compounds suitable for electron transport layers of organic light emitting diodes and to organic light emitting diodes including organic layers comprising the imidazopyridine-based compounds.

2. Description of the Related Art

Organic Light emitting diodes (OLEDs) are self-emitting diodes having wide viewing angles, excellent contrast, and quick response times.

Further, organic light emitting diodes have good luminance, operating voltage and response times, and can realize multicolor images.

In a conventional organic light emitting diode, an anode is formed on a substrate, and a hole transport layer, an emissive layer, an electron transport layer and a cathode are sequentially formed on the anode. The hole transport layer, the emissive layer and the electron transport layer are organic thin films formed of organic compounds. An organic light emitting diode having such a structure operates as follows. When a voltage is applied to the anode and cathode, holes injected from the anode migrate to the emissive layer via the hole transport layer. The electrons injected from the cathode migrate to the emissive layer via the electron transport layer. The holes and the electrons recombine with each other in the emissive layer to generate excitons. When the excitons drop from an excited state to a ground state, fluorescent molecules of the emissive layer emit light. Heteroaromatic compounds such as oxidiazoles, thiadiazoles, pyrimidines and the like may be used as the material for forming the electron transport layer. However, conventional organic light emitting diodes do not have satisfactory driving voltages, luminance, current densities, power efficiencies, life-times and the like.

SUMMARY OF THE INVENTION

According to one embodiment of the present invention, an imidazopyridine-based compound has high electron transport capabilities.

In another embodiment of the present invention, an organic light emitting diode using the imidazopyridine-based compound has high efficiency, low driving voltage, high luminance and a long life-time.

According to an embodiment of the present invention, an imidazopyridine-based compound includes a compound represented by Formula 1 below.

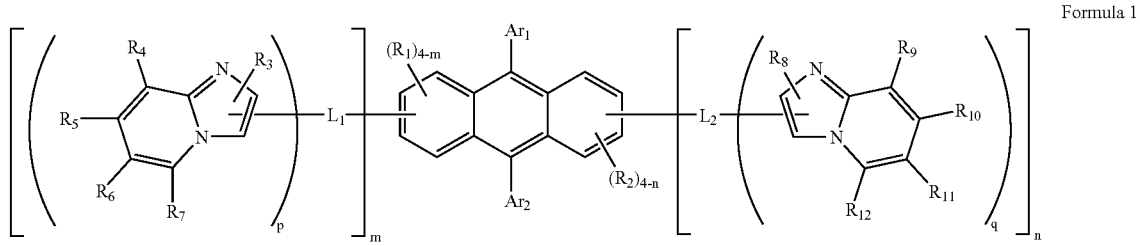

Formula 1

In Formula 1, p and q are each independently selected from integers ranging from 1 to 5, m and n are each independently selected from integers ranging from 0 to 4, and both m and n are not 0. $R_1, R_2, R_3, R_4, R_5, R_6, R_7, R_8, R_9, R_{10}, R_{11}$ and $R_{12}$ are each independently selected from hydrogen atoms, halogen atoms, hydroxyl groups, cyano groups, substituted or unsubstituted $C_1$-$C_{30}$ alkyl groups, substituted or unsubstituted $C_1$-$C_{30}$ alkoxy groups, substituted or unsubstituted $C_1$-$C_{30}$ acyl groups, substituted or unsubstituted $C_2$-$C_{30}$ alkenyl groups, substituted or unsubstituted $C_2$-$C_{30}$ alkynyl groups, substituted or unsubstituted $C_6$-$C_{30}$ aryl groups, and substituted or unsubstituted $C_3$-$C_{30}$ heteroaryl groups. At least two of $R_4, R_5, R_6$ and $R_7$ are bound to each other to form a saturated or unsaturated ring. At least two of $R_9, R_{10}, R_{11}$ and $R_{12}$ are bound to each other to form a saturated or unsaturated ring. $L_1$ and $L_2$ may each be independently selected from single bonds, substituted or unsubstituted $C_1$-$C_{30}$ alkylene groups, substituted or unsubstituted $C_6$-$C_{30}$ arylene groups, and substituted or unsubstituted $C_3$-$C_{30}$ heteroarylene groups. $Ar_1$ and $Ar_2$ may each be independently selected from substituted or unsubstituted $C_6$-$C_{30}$ aryl groups, and substituted or unsubstituted $C_3$-$C_{30}$ heteroaryl groups.

According to another embodiment of the present invention, an organic light emitting diode (OLED) comprises a first electrode, a second electrode, and an organic layer between the first second electrodes, the organic layer including the imidazopyridine-based compound.

The imidazopyridine-based compounds represented by Formula 1 have high electron transporting abilities, enabling organic light emitting diodes including organic layers having an imidazopyridine-based compound to have low driving voltages, high current densities, high luminance, high efficiencies and long life-times.

BRIEF DESCRIPTION OF THE DRAWINGS

The above and other features and advantages of the present invention will become more apparent by reference to the following detailed description when considered in conjunction with the attached drawings in which.

DETAILED DESCRIPTION OF THE INVENTION

Figure 1:
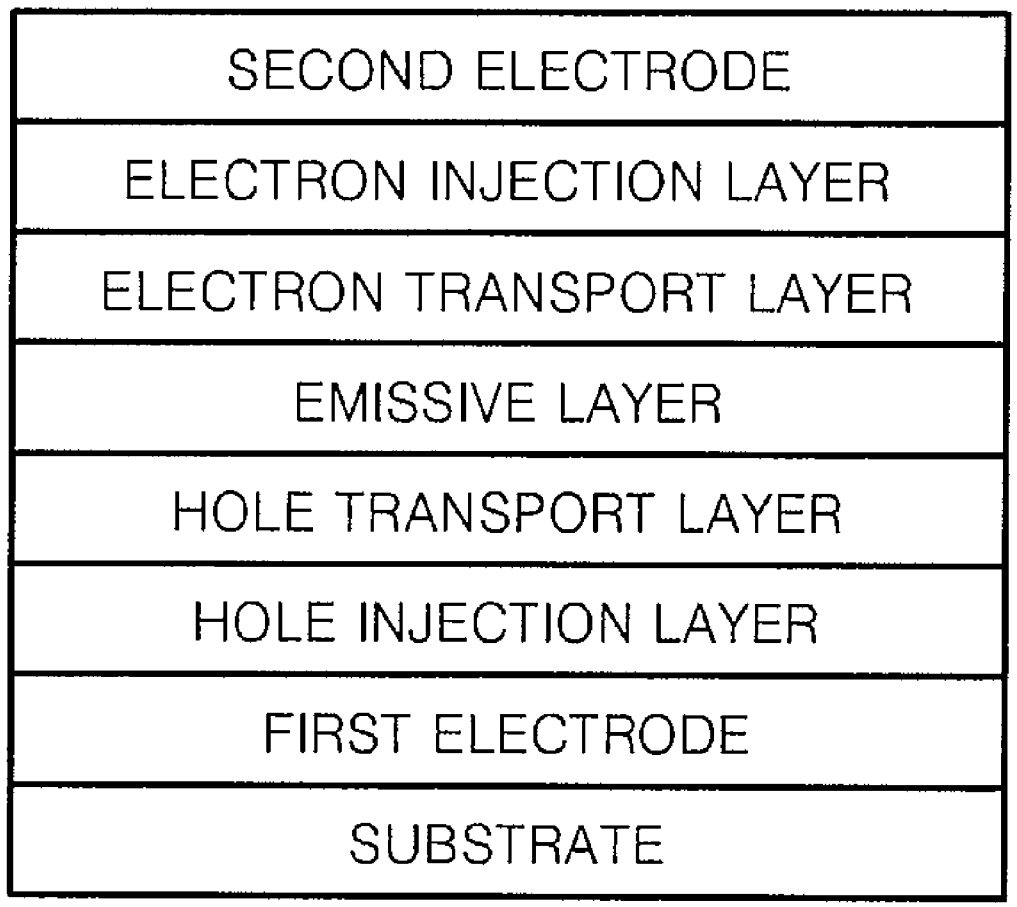
FIG. 1 is a schematic illustrating an organic light emitting diode according to an embodiment of the present invention.

An imidazopyridine-based compound according to an embodiment of the present invention is represented by Formula 1 below.

of the anthracene ring. Accordingly, the imidazopyridine-based compound can have improved structural stability and electron mobility.

In Formula 1, $R_1$, $R_2$, $R_3$, $R_4$, $R_5$, $R_6$, $R_7$, $R_8$, $R_9$, $R_{10}$, $R_{11}$ and $R_{12}$ are each independently selected from hydrogen atoms, halogen atoms, hydroxyl groups, cyano groups, substituted or unsubstituted $C_1$-$C_{30}$ alkyl groups, substituted or unsubstituted $C_1$-$C_{30}$ alkoxy groups, substituted or unsubstituted $C_1$-$C_{30}$ acyl groups, substituted or unsubstituted $C_2$-$C_{30}$ alkenyl groups, substituted or unsubstituted $C_2$-$C_{30}$ alkynyl groups, substituted or unsubstituted $C_6$-$C_{30}$ aryl groups, and substituted or unsubstituted $C_3$-$C_{30}$ heteroaryl groups. At least two of $R_4$, $R_5$, $R_6$ and $R_7$ are bound to each other to form a saturated or unsaturated ring, and at least two of $R_9$, $R_{10}$, $R_{11}$ and $R_{12}$ are bound to each other to form a saturated or unsaturated ring.

In one embodiment, $R_1$ through $R_{12}$ may each be independently selected from hydrogen atoms, substituted or unsubstituted $C_1$-$C_{10}$ alkyl groups, substituted or unsubstituted $C_2$-$C_{10}$ alkenyl groups, substituted or unsubstituted $C_6$-$C_{12}$ aryl groups, and substituted or unsubstituted $C_3$-$C_{12}$ heteroaryl groups.

According to another embodiment, at least two of $R_4$, $R_5$, $R_6$ and $R_7$, or at least two of $R_9$, $R_{10}$, $R_{11}$ and $R_{12}$, are bound to one another to form a substituted or unsubstituted $C_6$-$C_{12}$ aromatic ring.

In Formula 1, $L_1$ and $L_2$ may each be independently selected from single bonds, substituted or unsubstituted

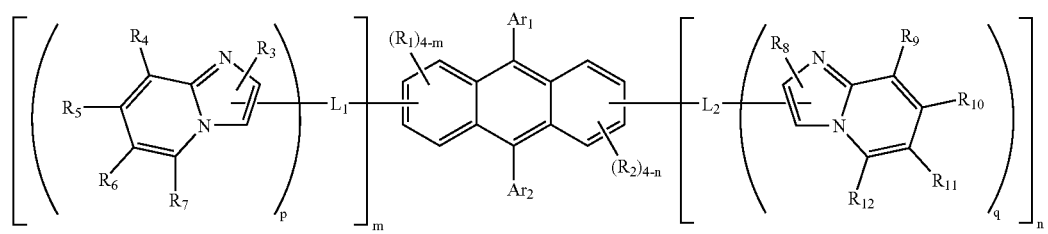

Formula 1

As shown in Formula 1, $L_1$ or $L_2$ bind an imidazopyridine ring to at least one of the 1$^{st}$ through 8$^{th}$ positions of an anthracene ring, but not to the 9$^{th}$ or 10$^{th}$ position of the ring. The imidazopyridine ring is not bound to the 9$^{th}$ or 10$^{th}$ position of the anthracene ring because the 9$^{th}$ and 10$^{th}$ positions are structurally weak points. Thus, when the 9$^{th}$ and 10$^{th}$ positions of the anthracene ring are substituted with a group having a specific function, the group can be easily decomposed from the anthracene ring by heat, oxygen, moisture or the like. For example, when an imidazopyridine ring (which is electron deficient) is bound to the 9$^{th}$ or 10$^{th}$ position of the anthracene ring, the imidazopyridine ring can be easily decomposed from the anthracene ring by heat generated during formation of the organic layer (for example, by deposition or the like) of an organic light emitting diode (OLED). The imidazopyridine ring can also be decomposed from the anthracene ring during operation of the organic light emitting diode, thus deteriorating the characteristics of the organic light emitting diode. However, in the imidazopyridine-based compound according to one embodiment of the present invention, an aromatic ring such as an aryl group or a heteroaryl group is bound to the 9$^{th}$ or 10$^{th}$ position of the anthracene ring. In addition, an imidazopyridine ring (which is electron deficient) is bound to at least one of the 1$^{st}$ through 8$^{th}$ positions $C_1$-$C_{30}$ alkylene groups, substituted or unsubstituted $C_6$-$C_{30}$ arylene groups, and substituted or unsubstituted $C_3$-$C_{30}$ heteroarylene groups. In one embodiment, for example, $L_1$ and $L_2$ may each be independently selected from substituted or unsubstituted $C_6$-$C_{12}$ arylene groups, and substituted or unsubstituted $C_3$-$C_{12}$ heteroarylene groups.

In Formula 1, $Ar_1$ and $Ar_2$ may each be independently selected from substituted or unsubstituted $C_6$-$C_{30}$ aryl groups, and substituted or unsubstituted $C_3$-$C_{30}$ heteroaryl groups. In one embodiment, for example, $Ar_1$ and $Ar_2$ may each be independently selected from substituted or unsubstituted $C_6$-$C_{12}$ aryl groups, and substituted or unsubstituted $C_3$-$C_{12}$ heteroaryl groups.

In Formula 1, p and q are each independently selected from integers ranging from 1 to 5. In one embodiment, for example, p and q are each integers ranging from 1 to 3. That is, at least one imidazopyridine ring can be bound to $L_1$ or $L_2$, which can be determined by the chemical structure of $L_1$ or $L_2$.

In Formula 1, m and n are each independently selected from integers ranging from 0 to 4, but both m and n are not 0. That is, in an imidazopyridine-based compound according to one embodiment of the present invention, at least one of the 1$^{st}$ through 8$^{th}$ positions of the anthracene ring is bound to an imidazopyridine ring. In one embodiment, for example, m may be 0, and n may be 1. In another embodiment, both m and n may be 1.

Nonlimiting examples of suitable unsubstituted $C_1$-$C_{30}$ alkyl groups for use in the compounds represented by Formula 1 include methyl groups, ethyl groups, propyl groups, isobutyl groups, sec-butyl groups, pentyl groups, iso-amyl groups, hexyl groups, and the like. At least one hydrogen atom of the alkyl group may be substituted with a substituent selected from halogen atoms, hydroxyl groups, nitro groups, cyano groups, amino groups, amidino groups, hydrazine, hydrazone, carboxyl groups or salts thereof, sulfonic acid groups or salts thereof, phosphoric acid groups or salts thereof, $C_1$-$C_{30}$ alkyl groups, $C_1$-$C_{30}$ alkenyl groups, $C_1$-$C_{30}$ alkynyl groups, $C_6$-$C_{30}$ aryl groups, $C_7$-$C_{20}$ arylalkyl groups, $C_2$-$C_{20}$ heteroaryl groups and $C_3$-$C_{30}$ heteroarylalkyl groups.

Nonlimiting examples of suitable unsubstituted $C_1$-$C_{30}$ alkoxy groups for use in compounds represented by Formula 1 include methoxy groups, ethoxy groups, phenyloxy groups, cyclohexyloxy groups, naphthyloxy groups, isopropyloxy groups, diphenyloxy groups and the like. At least one hydrogen atom of the alkoxy group can be substituted with a substituent selected from those discussed above with respect to the $C_1$-$C_{30}$ alkyl groups.

Nonlimiting examples of suitable unsubstituted $C_1$-$C_{30}$ acyl groups for use in compounds represented by Formula 1 include acetyl groups, ethylcarbonyl groups, isopropylcarbonyl groups, phenylcarbonyl groups, naphthylenecarbonyl groups, diphenylcarbonyl groups, cyclohexylcarbonyl groups, and the like. At least one hydrogen atom of the $C_1$-$C_{30}$ acyl group can be substituted with a substituent selected from those discussed above with respect to the $C_1$-$C_{30}$ alkyl groups.

Nonlimiting examples of suitable unsubstituted $C_2$-$C_{30}$ alkenyl groups for use in the compounds represented by Formula 1 include compounds containing a carbon-carbon double bond in the middle or end of an alkyl group defined above. For example, the unsubstituted $C_2$-$C_{30}$ alkenyl group may be selected from ethylene groups, propylene groups, butylene groups, hexylene groups, and the like. At least one hydrogen atom of the alkenyl group can be substituted with a substituent selected from those discussed above with respect to the $C_1$-$C_{30}$ alkyl groups.

Nonlimiting examples of suitable unsubstituted $C_2$-$C_{30}$ alkynyl groups for use in compounds represented by Formula 1 include compounds containing a carbon-carbon triple bond in the middle or end of an alkyl group defined above. For example, the unsubstituted $C_2$-$C_{30}$ alkynyl group may be selected from acetylene groups, propylene groups, phenylacetylene groups, naphthylacetylene groups, isopropylacetylene groups, t-butylacetylene groups, diphenylacetylene groups, and the like. At least one hydrogen atom of the alkynyl group can be substituted with a substituent selected from those discussed above with respect to the $C_1$-$C_{30}$ alkyl groups.

Nonlimiting examples of suitable unsubstituted $C_6$-$C_{30}$ aryl groups for use in compounds represented by Formula 1 include $C_6$-$C_{30}$ carbocyclic aromatic systems containing at least one aromatic ring. The at least one aromatic ring can include at least two rings fused with each other, or bound to each other by a single bond, or the like. At least one hydrogen atom of the aryl group can be substituted with a substituent selected from those discussed above with respect to the $C_1$-$C_{30}$ alkyl groups.

The substituted or unsubstituted $C_6$-$C_{30}$ aryl group can be selected from phenyl groups, $C_1$-$C_{10}$ alkylphenyl groups (for example, an ethylphenyl group), $C_1$-$C_{10}$ alkylbiphenyl groups (for example, an methylbiphenyl group), halophenyl groups (for example, o-, m- and p-fluorophenyl groups, and dichlorophenyl groups), dicyanophenyl groups, trifluoro methoxy phenyl groups, o-, m-, and p-tolyl groups, o-, m- and p-cumenyl groups, mesityl groups, phenoxy phenyl groups, (α,α-dimethylbenzyl)phenyl groups, (N,N'-dimethyl)aminophenyl groups, (N,N'-diphenyl)aminophenyl groups, pentalenyl groups, indenyl groups, naphthyl groups, halonaphthyl groups (for example, a fluoronaphthyl group), $C_1$-$C_{10}$ alkylnaphthyl groups (for example, a methylnaphthyl group), $C_1$-$C_{10}$ alkoxynaphthyl groups (for example, a methoxynaphthyl group), anthracenyl groups, azulenyl groups, heptalenyl groups, acenaphthylenyl groups, phenalenyl groups, fluorenyl groups, anthraquinolyl groups, methylanthryl groups, phenanthrenyl groups, triphenylene groups, pyrenyl groups, chrysenyl groups, ethyl-chrysenyl groups, picenyl groups, perylenyl groups, chloroperylenyl groups, pentaphenyl groups, pentacenyl groups, tetraphenylenyl groups, hexaphenyl groups, hexacenyl groups, rubicenyl groups, coronenyl groups, trinaphthylenyl groups, heptaphenyl groups, heptacenyl groups, pyranthrenyl groups, ovalenyl groups, and the like.

Nonlimiting examples of suitable unsubstituted $C_3$-$C_{30}$ heteroaryl groups for use in compounds represented by Formula 1 include systems having at least one aromatic ring that includes at least one hetero atom selected from N, O, P and S, where the remaining ring member is carbon. The at least one aromatic ring can be at least two rings that are fused with each other, or bound to each other by a single bond, or the like. At least one hydrogen atom of the heteroaryl group can be substituted with a substituent selected from those discussed above with respect to the $C_1$-$C_{30}$ alkyl groups.

Nonlimiting examples of suitable unsubstituted $C_3$-$C_{30}$ heteroaryl groups for use in compounds represented by Formula 1 include pyrazolyl groups, imidazolyl groups, oxazolyl groups, thiazolyl groups, triazolyl groups, tetrazolyl groups, oxadiazolyl groups, pyridinyl groups, pyridazinyl groups, pyrimidinyl groups, triazinyl groups, carbazolyl groups, indolyl groups, quinolinyl groups, isoquinolinyl groups, and the like.

Nonlimiting examples of suitable substituents for $R_1$ through $R_{12}$ of Formula 1 include hydrogen atoms, $C_1$-$C_{10}$ alkyl groups, $C_1$-$C_{10}$ haloalkyl groups, $C_2$-$C_{10}$ alkenyl groups, $C_2$-$C_{10}$ haloalkenyl groups, phenyl groups, halophenyl groups, $C_1$-$C_{10}$ alkylphenyl groups, $C_1$-$C_{10}$ alkoxyphenyl groups, naphthyl groups, halonaphthyl groups, $C_1$-$C_{10}$ alkylnaphthyl groups, and $C_1$-$C_{10}$ alkoxynaphthyl groups.

Nonlimiting examples of suitable substituents for $L_1$ and $L_2$ of Formula 1 include phenylene groups, halophenylene groups, $C_1$-$C_{10}$ alkylphenylene groups, $C_1$-$C_{10}$ alkoxyphenylene groups, naphthylene groups, halonaphthylene groups, $C_1$-$C_{10}$ alkylnaphthalene groups, and $C_1$-$C_{10}$ alkoxynaphthylene groups.

Nonlimiting examples of suitable substituents for $Ar_1$ and $Ar_2$ of Formula 1 include phenyl groups, halophenyl groups, $C_1$-$C_{10}$ alkylphenyl groups, $C_1$-$C_{10}$ alkoxyphenyl groups, naphthyl groups, halonaphthyl groups, $C_1$-$C_{10}$ alkylnaphthyl groups, $C_1$-$C_{10}$ alkoxynaphthyl groups, pyridinyl groups, halopyridinyl groups, $C_1$-$C_{10}$ alkylpyridinyl groups, $C_1$-$C_{10}$ alkoxypyridinyl groups, quinolinyl groups, haloquinolinyl groups, $C_1$-$C_{10}$ alkylquinolinyl groups, $C_1$-$C_{10}$ alkoxyquinolinyl groups, isoquinolinyl groups, haloisoquinolinyl groups, $C_1$-$C_{10}$ alkylisoquinolinyl groups, and $C_1$-$C_{10}$ alkoxyisoquinolinyl groups.

In one embodiment, the imidazopyridine-based compound may be represented by one of Formulae 1a, 1b, 1c and 1d.

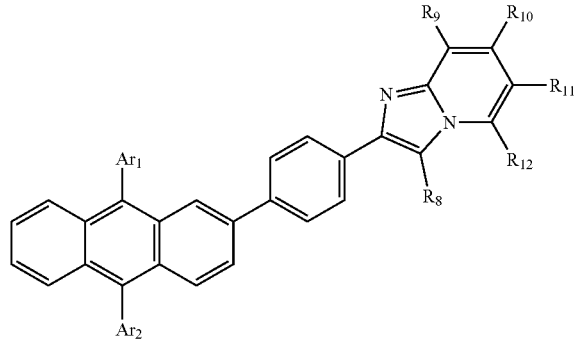
Formula 1a
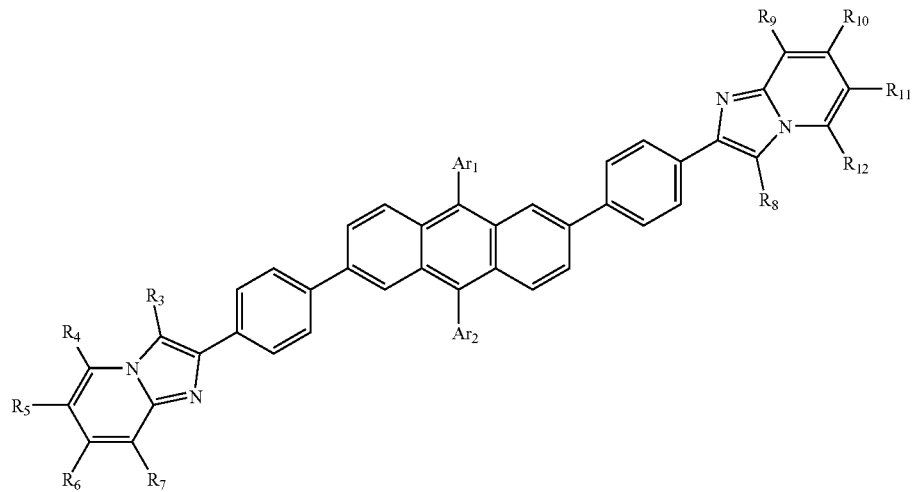
Formula 1b
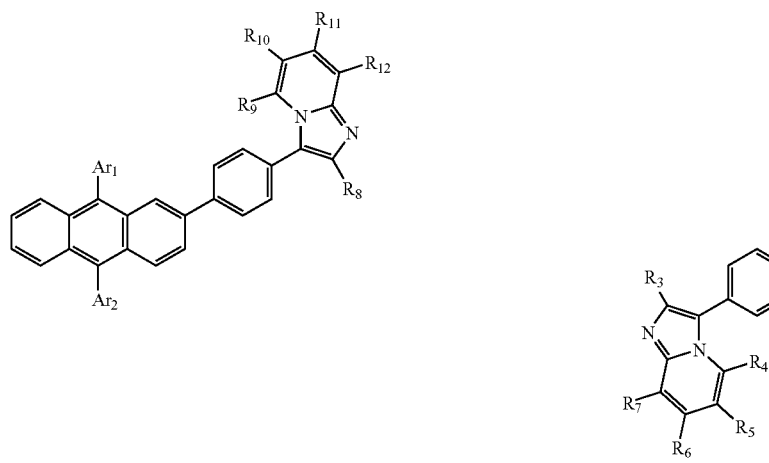
Formula 1c
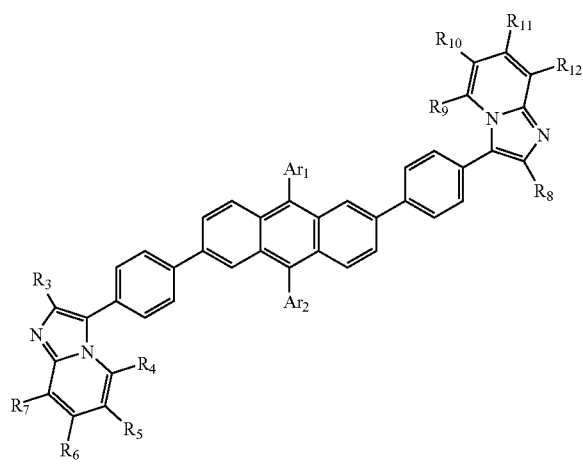
Formula 1d
In Formulae 1a through 1d, $R_3$ through $R_{12}$, $Ar_1$ and $Ar_2$ are the same as described above with respect to Formula 1.
Nonlimiting examples of suitable compounds for use as the imidazopyridine-based compound represented by Formula 1 include Compounds 1 through 11 below.

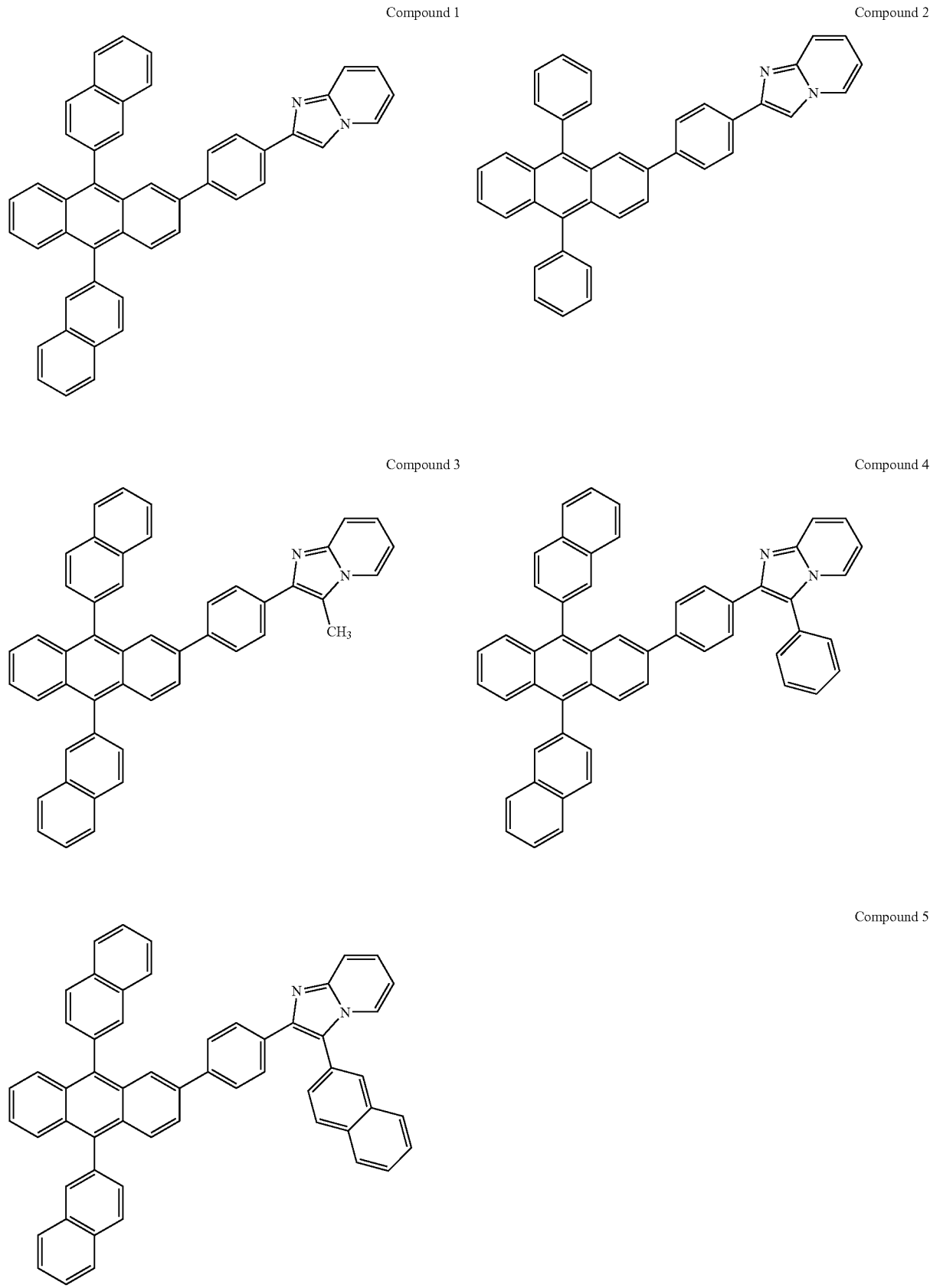

-continued
Compound 6
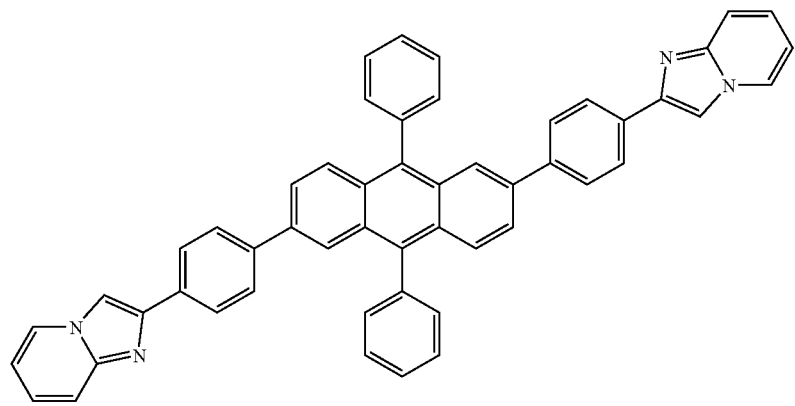
Compound 7 Compound 8
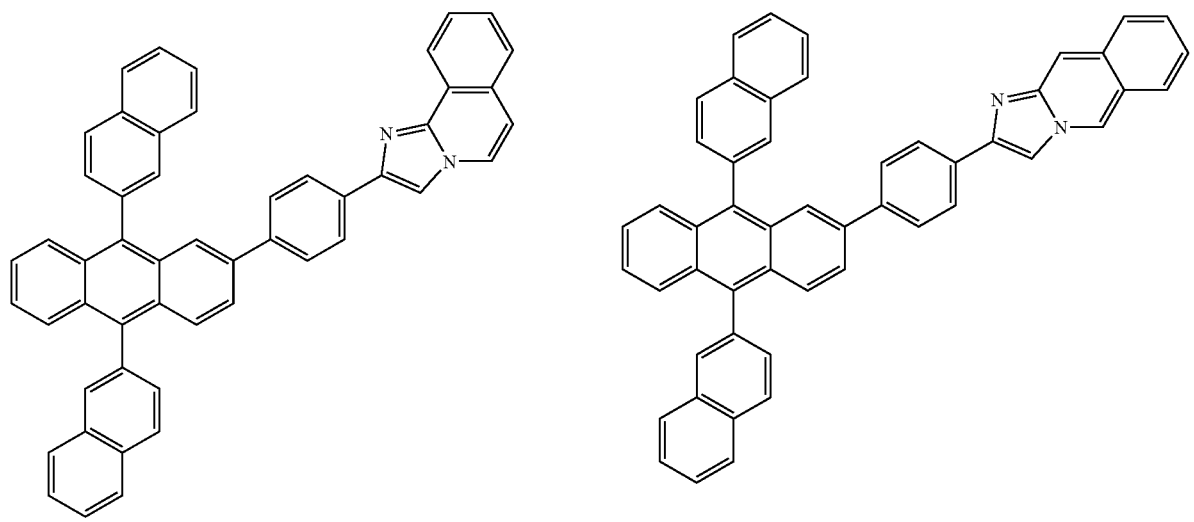
Compound 9 Compound 10
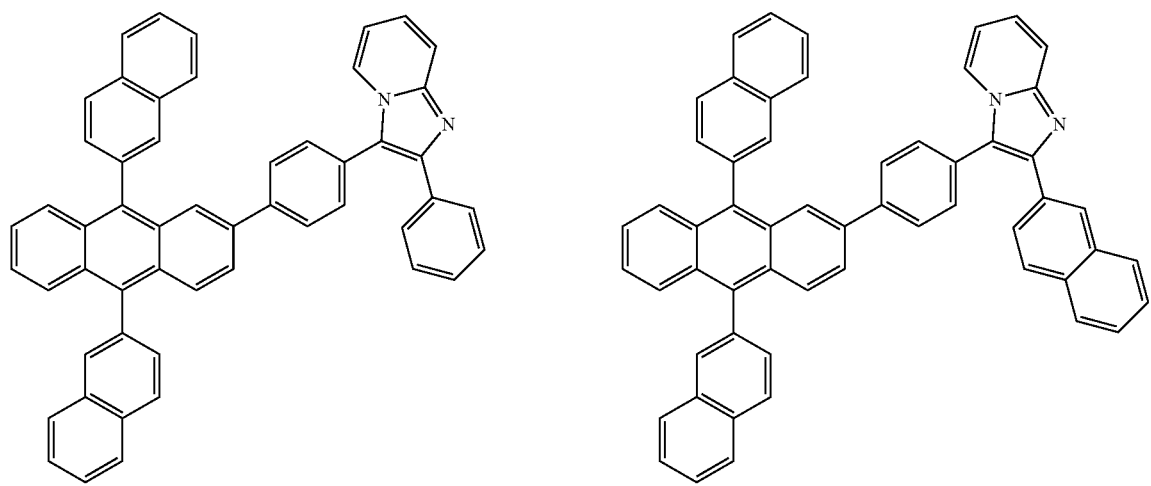

-continued

Compound 11

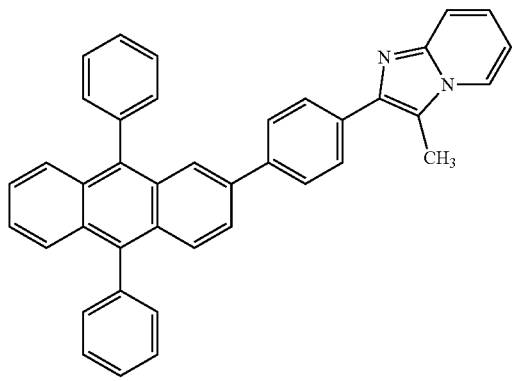

The imidazopyridine-based compound represented by Formula 1 can be prepared using various methods. For example, the imidazopyridine-based compound represented by Formula 1 can be obtained by reacting a compound represented by Formula 2 below with at least one of a compound represented by Formula 3 and a compound represented by Formula 4, both shown below.

Formula 2

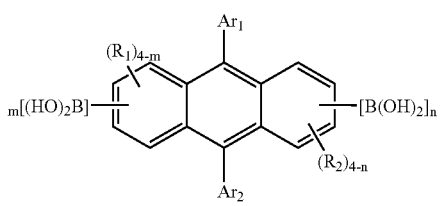

Formula 3

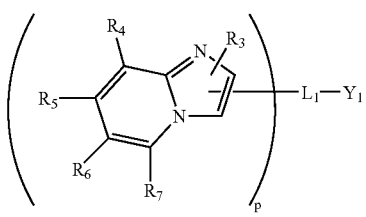

Formula 4

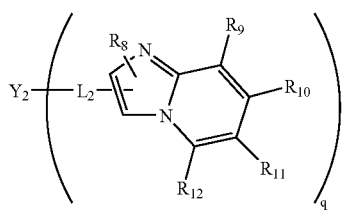

In Formulae 2 through 4, $R_1$ through $R_{12}$, $L_1$, $L_2$, $Ar_1$, $Ar_2$, p, q, n and m are the same as defined above. The imidazopyridine-based compound represented by Formula 1 can be prepared by a Suzuki reaction method.

According to one embodiment of the present invention, an imidazopyridine-based compound represented by Formula 1 can be used to form an organic layer of an organic light emitting diode. In one embodiment, for example, an organic light emitting diode includes a first electrode, a second electrode, and an organic layer including an imidazopyridine-based compound represented by Formula 1 between the first and second electrodes. According to one embodiment, the organic layer may be an electron transport layer. The organic light emitting diode may further include a layer selected from a hole injection layer, a hole transport layer, an electron blocking layer, an emissive layer, a hole blocking layer, an electron transport layer, an electron injection layer, and combinations thereof. For example, when the organic layer including an imidazopyridine-based compound represented by Formula 1 is an electron transport layer, the organic light emitting diode may further include a hole injection layer, a hole transport layer, an emissive layer and an electron injection layer. In addition, when the emissive layer is formed of a phosphorous material, the organic light emitting diode may further include a hole blocking layer. The organic light emitting diode may have various other structures.

FIG. 1 illustrates a structure of the organic light emitting diode according to one embodiment of the present invention. The organic light emitting diode illustrated in FIG. 1 has a first electrode/hole injection layer/hole transport layer/emissive layer/electron transport layer/electron injection layer/second electrode structure. However, it is understood that the organic light emitting diode is not limited to this structure and may have various other structures, such as a first electrode/hole injection layer/emissive layer/electron transport layer/electron injection layer/second electrode structure, or a first electrode/hole injection layer/hole transport layer/emissive layer/hole blocking layer/electron transport layer/electron injection layer/second electrode structure. The electron transport layer can be formed of an imidazopyridine-based compound represented by Formula 1.

According to one embodiment of the present invention, the emissive layer of the organic light emitting diode may include a red, green, blue or white phosphorescent or fluorescent dopant. The phosphorescent dopant may be an organic metal compound which contains a metal selected from Ir, Pt, Os, Ti, Zr, Hf, Eu, Tb, Tm, and combinations thereof.

Hereinafter, a method of manufacturing an organic light emitting diode according to an embodiment of the present invention will be described with reference to the organic light emitting device illustrated in FIG. 1. First, a first electrode is formed by depositing or sputtering a high work-function material on a substrate. The first electrode can be an anode or a cathode. The substrate, which can be any substrate used in conventional organic light emitting devices, may be a glass substrate or a transparent plastic substrate that can be easily treated, is waterproof, and has excellent mechanical strength, thermal stability, transparency, and surface smoothness. The first electrode can be formed of ITO, IZO, $SnO_2$, ZnO, or any transparent material that has high conductivity.

Next, a hole injection layer (HIL) can be formed on the first electrode by vacuum deposition, spin coating, casting, Langmuir Blodgett (LB) deposition, or the like. When the HIL is formed by vacuum deposition, the vacuum deposition conditions may vary depending on the compound used to form the HIL, and the desired structure and thermal properties of the HIL to be formed. In general, however, vacuum deposition may be performed at a deposition temperature ranging from about 100° C. to about 500° C., a pressure ranging from about $10^{-8}$ to about $10^{-3}$ torr, a deposition speed ranging from about 0.01 to about 100 Å/sec. The thickness of the vacuum deposited layer may range from about 10 Å to about 5 µm.

When the HIL is formed by spin coating, coating conditions may vary depending on the compound used to form the HIL, and the desired structure and thermal properties of the HIL to be formed. In general, however, the coating speed may range from about 2,000 to about 5,000 rpm, and the temperature for heat treatment (which is performed to remove solvent after coating) may range from about 80 to about 200° C.

The HIL material is not particularly limited and can be any known material used to form HILs. Nonlimiting examples of suitable HIL materials include phthalocyanine compounds (such as copperphthalocyanine), star-burst type amine derivatives (such as TCTA (shown below), m-MTDATA (shown below), and m-MTDAPB), soluble and conductive polymers (such as polyaniline/Dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), (polyaniline)/poly(4-styrenesulfonate) (PANI/PSS)), and the like.

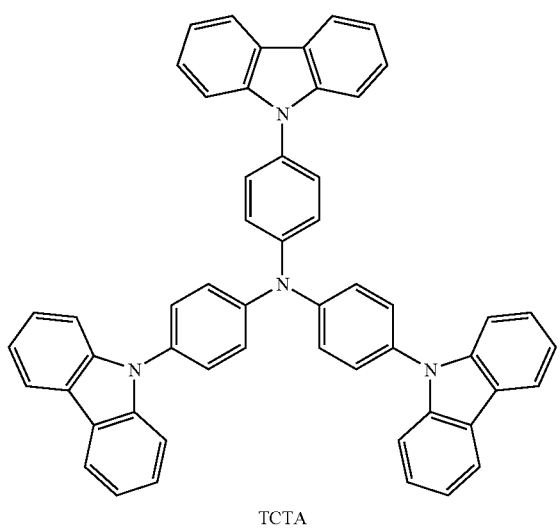

TCTA

-continued

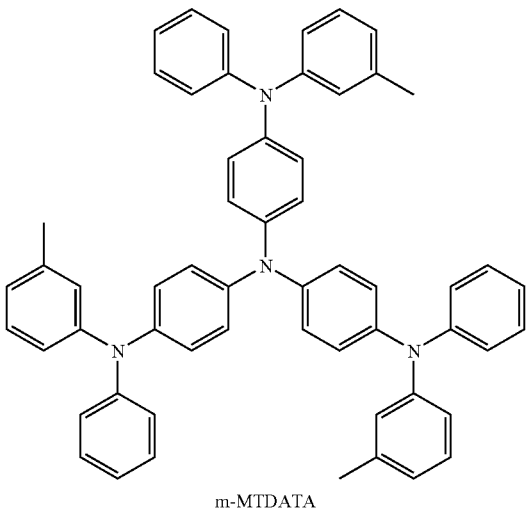

m-MTDATA

The thickness of the HIL may range from about 100 to about 10,000 Å. In one embodiment, for example, the thickness may range from about 100 to about 1,000 Å. When the thickness of the HIL is within the above described ranges, the HIL has excellent hole injecting abilities, and organic light emitting diodes having excellent driving voltages can be obtained.

A hole transport layer (HTL) can be formed on the HIL by vacuum deposition, spin coating, casting, LB deposition, or the like. When the HTL is formed by vacuum deposition or spin coating, the conditions for deposition and coating are similar to those for the formation of the HIL, although the deposition or coating conditions may vary according to the material used to form the HTL.

The HTL material is not particularly limited and can be any known material for use as a HTL. Nonlimiting examples of suitable HTL materials include carbazole derivatives (such as N-phenylcarbazole and polyvinylcarbazole), typical amine derivatives having aromatic condensation rings (such as N,N'-bis(3-methylphenyl)-N,N'-diphenyl-[1,1-biphenyl]-4, 4'-diamine (TPD shown below), and N,N'-di(naphthalene-1-yl)-N,N'-diphenyl benzydine (α-NPD shown below)), and the like.

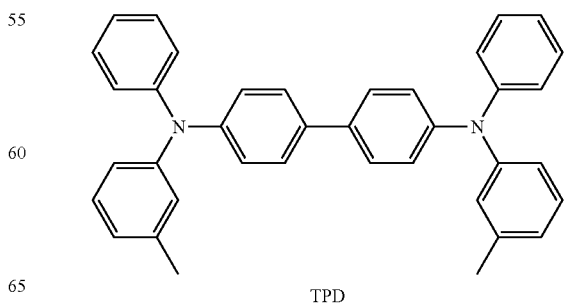

TPD

-continued

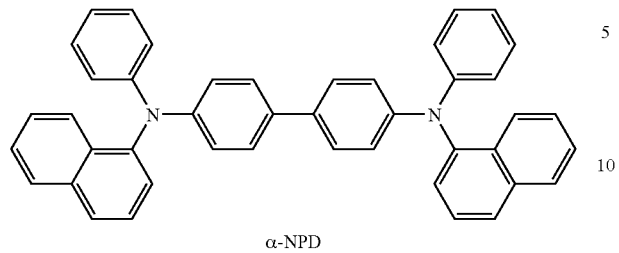

α-NPD

The thickness of the HTL may range from about 50 to about 1,000 Å. In one embodiment, for example, the thickness ranges from about 100 to about 600 Å. When the thickness of the HTL is within the above described ranges, the HTL has excellent hole transporting abilities, and organic light emitting diodes having excellent driving voltages can be obtained.

An emissive layer (EML) can be formed on the HTL by vacuum deposition, spin coating, casting, LB deposition, or the like. When the EML is formed by vacuum deposition or spin coating, the conditions for deposition and coating are similar to those for the formation of the HIL, although the deposition and coating conditions may vary according to the material used to form the EML.

The emissive layer can be formed of various known emissive materials, and can include known hosts and dopants. The dopant can be a known fluorescent dopant or a known phosphorescent dopant. Nonlimiting examples of suitable host materials include $Alq_3$, 4,4'-N,N'-dicarbazole-biphenyl (CBP), poly(n-vinylcarbazole) (PVK), distyrylarylene (DSA), and the like.

Nonlimiting examples of suitable fluorescent dopants include IDE102 and IDE105 obtained from Idemitsu Co. Nonlimiting examples of suitable phosphorescent dopants include green phosphorescent dopants (such as $Ir(ppy)_3$ (ppy is an abbreviation of phenylpyridine), (4,6-F2 ppy)$_2$Irpic, TEB002 obtained from Covion, Ltd.), red phosphorescent dopants (such as platinum(II) octaethylporphyrin (PtOEP)), compounds represented by Formula 5 below, Firpric, TBPe, and the like.

Formula 5

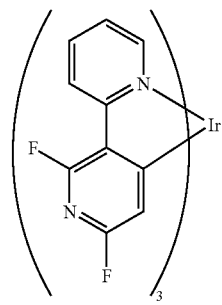

-continued

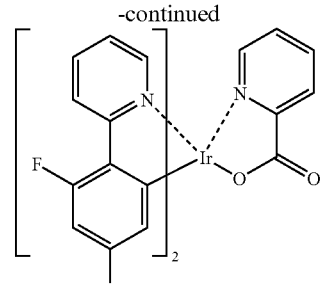

Firpic

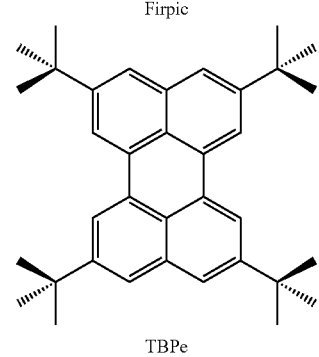

TBPe

The dopant may be present in an amount ranging from about 0.1 to about 20 parts by weight based on 100 parts by weight of the total weight of the emissive layer (that is, the total weight of the host and dopant). In one embodiment, the dopant is present in an amount ranging from about 0.5 to about 12 parts by weight. When the dopant is present in an amount greater than about 0.1 parts by weight, the effect of the addition of the dopant increases. Also, when the amount of either the phosphorescent or fluorescent dopant is less than about 20 parts by weight, concentration quenching can be substantially prevented.

The thickness of the EML may range from about 100 to about 1,000 Å. In one embodiment, for example, the thickness ranges from about 200 to about 600 Å. When the thickness of the EML is within these ranges, the EML has excellent emissive abilities, and organic light emitting diodes having excellent driving voltages can be obtained.

When the EML includes a phosphorescent dopant, a hole blocking layer (HBL) can be formed on the EML in order to prevent triplet excitons or holes from migrating into an electron transport layer (ETL) (not shown in FIG. 1). The HBL material is not particularly limited and can be any known material used to form HBLs. Nonlimiting examples of suitable HBL materials include oxadiazole derivatives, triazole derivatives, phenanthroline derivatives, Balq, BCP, and the like.

The thickness of the HBL may range from about 50 to about 1,000 Å. In one embodiment, for example, the thickness ranges from about 100 to about 300 Å. When the thickness of the HBL is within these ranges, the HBL has excellent hole blocking abilities, and organic light emitting devices having excellent driving voltages can be obtained.

An electron transport layer (ETL) may be formed on the HBL by vacuum deposition, spin coating, casting, or the like. When the ETL is formed by vacuum deposition or spin coating, the conditions for deposition and coating are, in general, similar to those for the formation of the HIL, although the deposition and coating conditions may vary according to the material used to form the ETL.

The ETL may be formed of an imidazopyridine-based compound represented by Formula 1. The ETL may also be formed of a quinoline derivative, for example, tris(8-quinolinorate)aluminum ($Alq_3$), TAZ, or the like, which are known in the art.

The thickness of the ETL may range from about 100 to about 1,000 Å. In one embodiment, for example, the thickness ranges from about 100 to about 500 Å. When the thickness of the ETL is within these ranges, the ETL has excellent electron transporting abilities, and organic light emitting diodes having excellent driving voltages can be obtained.

In addition, an electron injection layer (EIL) may be deposited on the ETL. The EIL makes it easy for electrons to be injected from a cathode.

The EIL may be formed of LiF, NaCl, CsF, $Li_2O$, BaO, or the like, which materials are known in the art. Deposition and coating conditions for formation of the EIL are, in general, similar to the conditions for the formation of the HIL, although they may vary according to the material used to form the EIL.

The thickness of the EIL may range from about 1 to about 100 Å. In one embodiment, for example, the thickness ranges from about 5 to about 90 Å. When the thickness of the EIL is within these ranges, the EIL has excellent electron injecting abilities, and organic light emitting diodes having excellent driving voltages can be obtained.

Finally, a second electrode can be formed on the EIL by vacuum deposition, sputtering, or the like. The second electrode can be used as a cathode or an anode. The second electrode may be formed of a low work-function metal, an alloy, an electrically conductive compound, or a combination thereof. Nonlimiting examples of suitable materials for the second electrode include Li, Mg, Al, Al—Li, Ca, Mg—In, Mg—Ag, and the like. Alternatively, a transparent cathode formed of ITO or IZO can be used to produce a front surface light emitting diode.

The following Synthesis Examples detailing the synthesis of Compounds 1, 4 and 7, and Examples detailing the making of organic light emitting diodes according to embodiments of the present invention are presented for illustrative purposes only and are not intended to limit the scope of the present invention.

SYNTHESIS EXAMPLE 1

Synthesis of Compound 1

Compound 1 was synthesized through Reaction Scheme 1 below:

Reaction Scheme 1

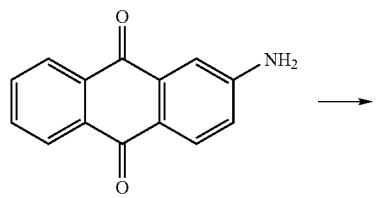

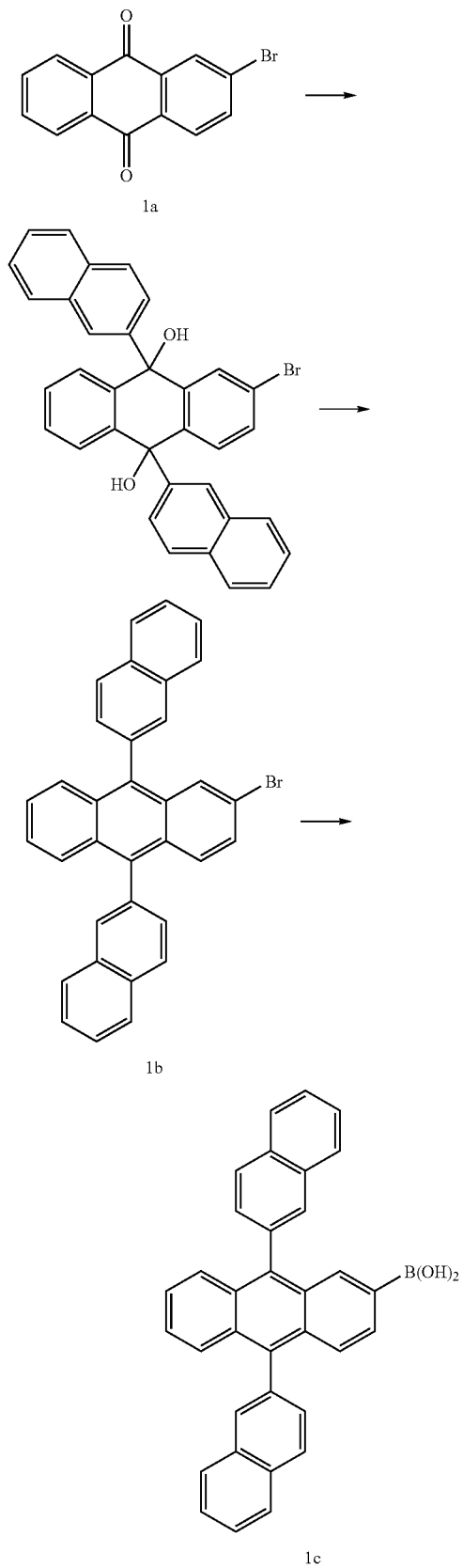

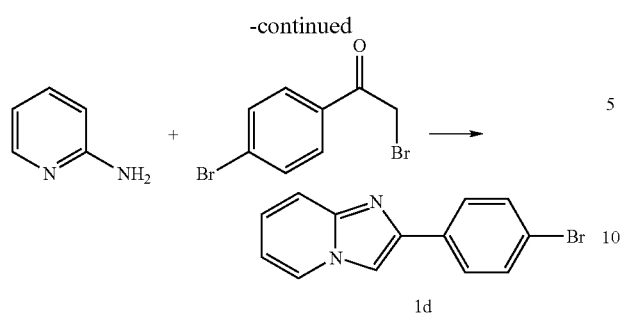

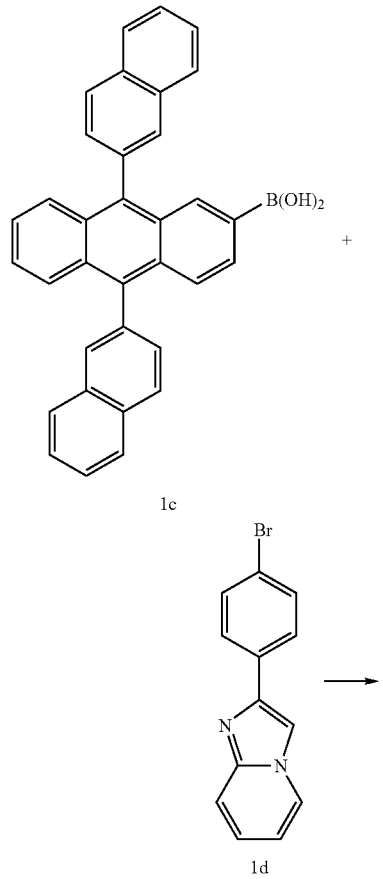

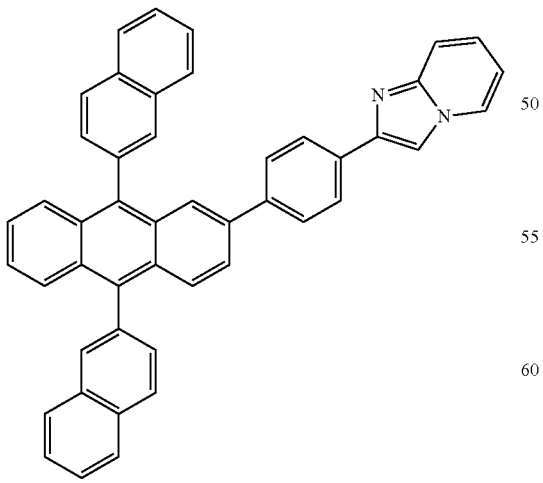

Compound 1

Synthesis of Intermediate 1a 10 g of copper bromide (44 mmol) and 8 g of 2-aminoanthraquinone (35.8 mmol) were added to 250 ml of bromic acid, and the mixture was heated at 65° C. After gas generation was terminated, the mixture was cooled to room temperature. Then, the mixture was added to 1,000 ml of 20% aqueous hydrochloric acid, and was extracted with dichloromethane. Moisture remaining in an organic layer was removed with anhydrous $MgSO_4$, and the resulting product was dried under pressure. The resulting product was purified by column chromatography (dichloromethane:normal hexane=4:1) to obtain 7.7 g of Intermediate 1a (yield 75%).

Synthesis of Intermediate 1b 10 g of Intermediate 1a (34.8 mmol) was added to 100 ml of THF dried under nitrogen atmosphere, and the temperature of the mixture was decreased to −78° C. 0.5 M of 2-naphthylmagnesiumbromide (10 mmol) was slowly added to the mixture. The temperature of the mixture was increased to room temperature and the mixture was stirred for 3 hours. An aqueous ammonium chloride solution was added to the reacted mixture, and then the resulting product was extracted with methylenechloride. An organic layer was dried using anhydrous $MgSO_4$ and the solvent was removed. The mixture obtained therefrom was dissolved with a small amount of ethylether. Then, petroleum ether was added to the mixture, and stirred for several hours to obtain a solid compound. The obtained solid compound was filtered and then vacuum dried to obtain 17.6 g of dinaphthyl dialcohol.

17.6 g of the dinaphthyl dialcohol (32.4 mmol) was dispersed in 200 ml of acetic acid under a nitrogen atmosphere. Then, 53.4 g of potassium iodide (330 mmol) and 58 g of sodium hypophosphite hydrate (660 mmol) were added to the mixture, and then stirred and refluxed for 3 hours. The resulting product was cooled to room temperature, filtered, washed with water and methanol, and then vacuum dried to obtain 11.3 g of light-yellow Intermediate 1b.

Synthesis of Intermediate 1c 5 g of Intermediate 1b (9.81 mmol) was dissolved in 70 ml of THF dried under nitrogen atmosphere, and 4.7 ml of lithium butyl (11.8 mmol) was added to the mixture at −78° C. The mixture was stirred for one hour at the same temperature, and then 2.20 ml of trimethyl borate (29.4 mmol) was added to the mixture. The temperature of the mixture was increased to room temperature, and one hour later, 2N of an aqueous hydrochloric acid solution was added to the mixture and stirred for 3 hours. The obtained solid compound was filtered while being washed with toluene to obtain 3.27 g of light-yellow Intermediate 1c (yield 70%).

Synthesis of Intermediate 1d 3.39 g of 2-aminopyridine (35.98 mmol) and 10 g of 2,4'-dibromo acetophenone (35.98 mmol) were dissolved in 150 ml of ethanol, and the mixture was refluxed for 12 hours. The mixture was cooled to room temperature to obtain a white solid. The obtained white solid was washed with a saturated NaHCO₃ solution. Moisture remaining in the organic layer was removed with anhydrous MgSO₄, dried under reduced pressure, and then recrystallized (dichloromethane/normal hexane) to obtain 8.02 g of Intermediate 1d having a plate crystalline form (yield 82%).

Synthesis of Compound 1

1.85 g of Intermediate 1c (3.90 mmol) and 1 g of Intermediate 1d (3.90 mmol) were added to a mixed solvent of 2.7 g of an aqueous potassium carbonate solution (19.5 mmol) and THF. 225 mg of Pd(PPh₃)₄ (19.5 mmol) was added to the mixture while the mixture was stirred, and the mixture was refluxed for 6 hours. The mixture was cooled to room temperature, and then the obtained solid compound was filtered while being washed with water, ethanol and THF to obtain 1.73 g of Compound 1 in the form of a pale yellow powder (yield 71%). (1H NMR (400 MHz, CDCl₃) 8.13-8.04 (7H), 8.01 (1H), 7.97-7.92 (4H), 7.86-7.82 (2H), 7.75 (2H), 7.71-7.58 (10H), 7.32 (2H), 7.15 (1H), 6.75 (1H)).

SYNTHESIS EXAMPLE 2

Synthesis of Compound 4

Compound 4 was synthesized through Reaction Scheme 2 below:

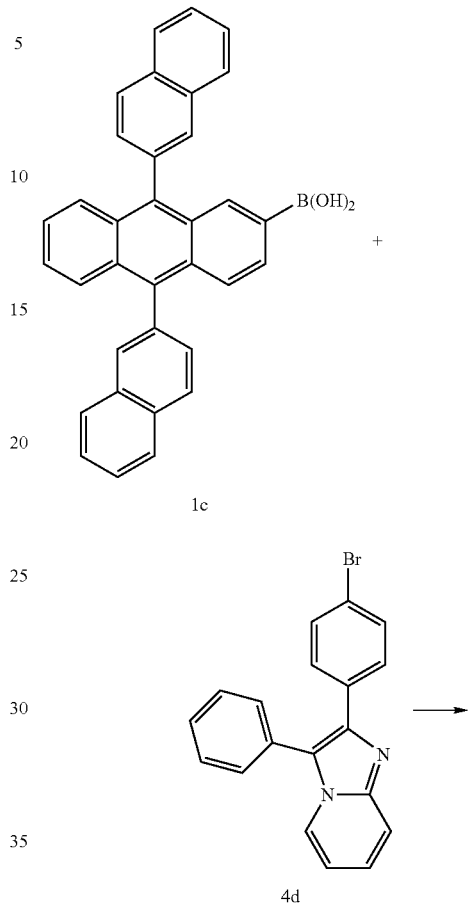

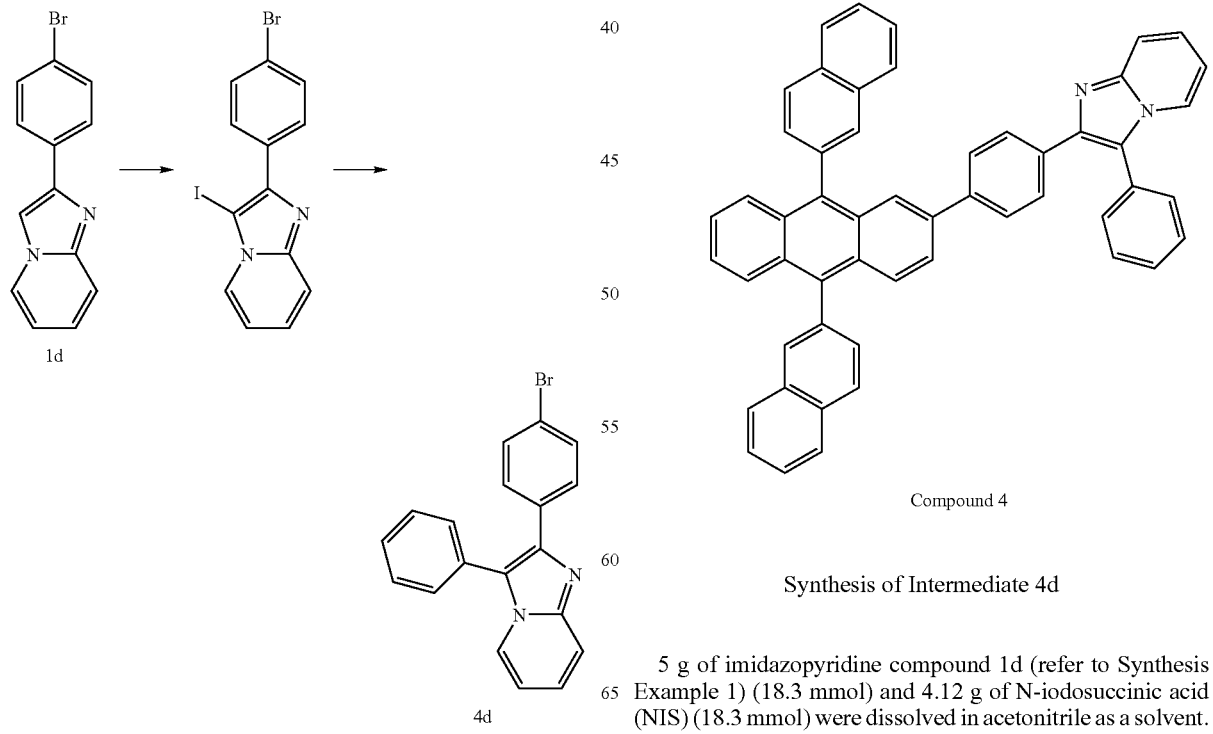

Synthesis of Intermediate 4d 5 g of imidazopyridine compound 1d (refer to Synthesis Example 1) (18.3 mmol) and 4.12 g of N-iodosuccinic acid (NIS) (18.3 mmol) were dissolved in acetonitrile as a solvent. The mixture was stirred at room temperature for one hour, and then 100 ml of chloroform was added thereto. The mixture was washed with 10% of an aqueous sodium hydroxide solution, and then washed with an aqueous saturated sodium thiosulfate solution and water and dried with anhydrous magnesium sulfate. Then, the resulting product was filtered and the solvent was removed. The obtained solid was washed with methanol and filtered to obtain 5.8 g of an iodo compound (yield 79%).

The obtained iodo compound and 1.76 g of phenylboronic acid (14.5 mmol) were added to a mixed solvent of 10 g of an aqueous potassium carbonate solution and THF. 335 mg of Pd(PPh$_3$)$_4$ was added to the mixture while the mixture was stirred and the mixture was refluxed for 24 hours. The resulting product was extracted with dichloromethane. Moisture remaining in the organic layer was removed with anhydrous MgSO$_4$ and dried under reduced pressure. The resulting product was purified by column chromatography (ethylacetate: normal hexane=2:3) to obtain 2.93 g of Intermediate 4d (yield 58%).

Synthesis of Compound 4

Compound 4 was prepared in the same manner as in Compound 1 according to Synthesis Example 1, except that Intermediate 4d was used instead of Intermediate 1d. 10 g of Intermediate 1c (21.08 mmol) and 6.69 g of Intermediate 4d (19.16 mmol) were subjected to a Suzuki reaction, yielding 9.72 g of Compound 4 in the form of a pale yellow powder (yield 73%). (1H NMR (400 MHz, CDCl$_3$) 8.08(1H), 8.03-8.01(2H), 7.97-7.88(3H), 7.81(1H), 7.74-7.58(12), 7.51-7.40(10), 7.29-7.23(3H), 7.15(1H), 6.69(1H)).

SYNTHESIS EXAMPLE 3

Synthesis of Compound 7

Compound 7 was synthesized through Reaction Scheme 3 below:

Reaction Scheme 3

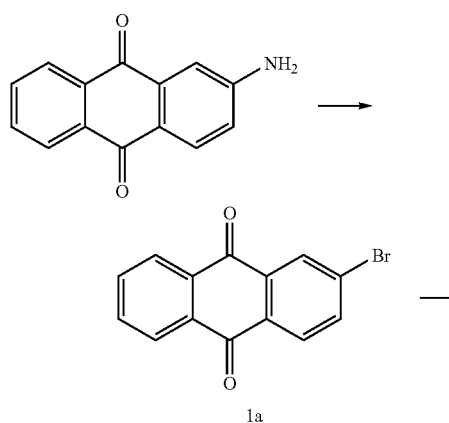

-continued

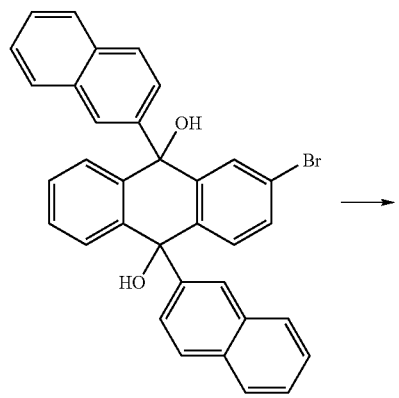

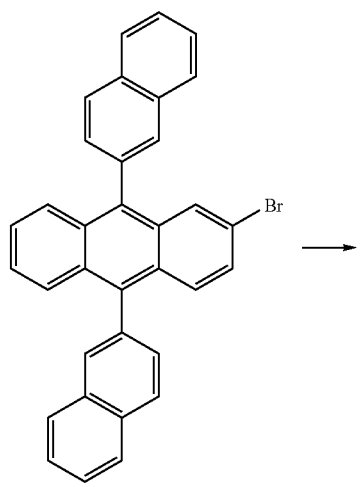

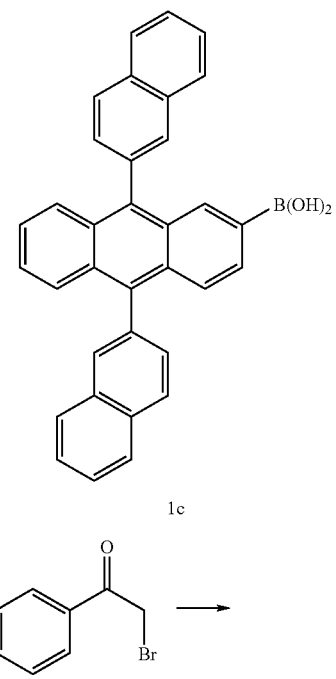

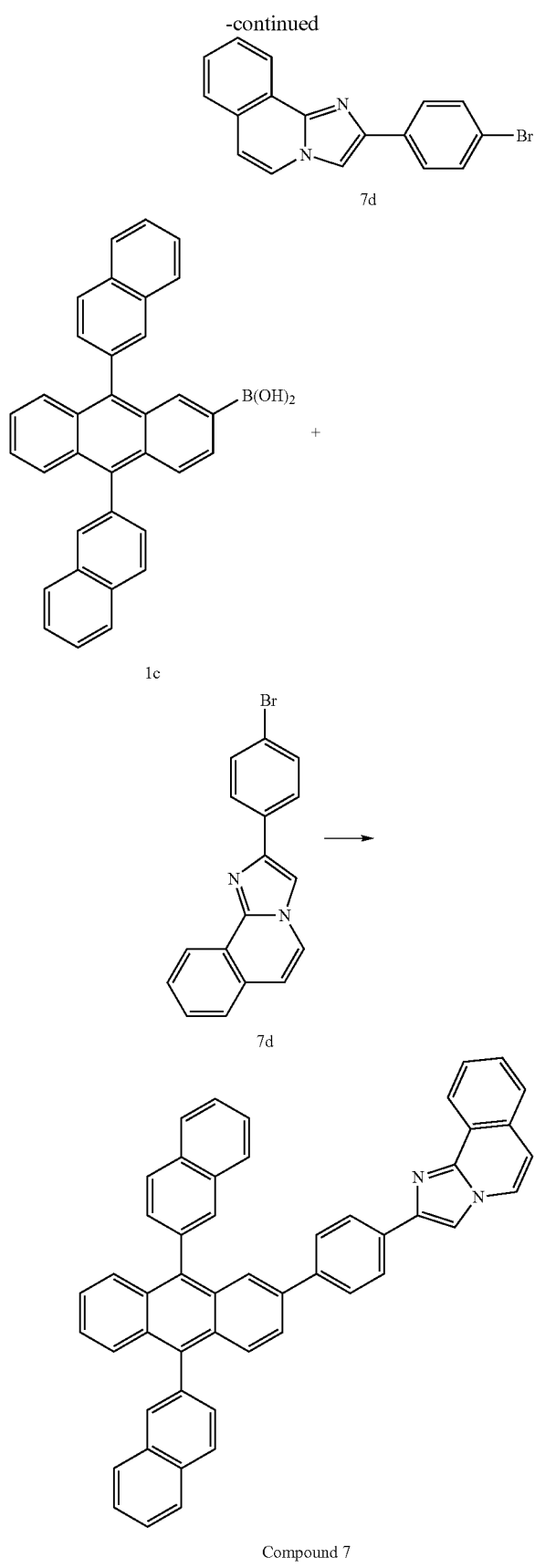

Compound 7 was prepared in the same manner as in Synthesis Example 1, except that Intermediate 7d was used instead of Intermediate 1d. Intermediate 7d was obtained using 1-aminoisoquinoline instead of 2-aminopyridine. 10 g of Intermediate 1c (21.08 mmol) and 6.19 g of Intermediate 7d (19.16 mmol) were subjected to a Suzuki reaction, yielding 9.03 g of Compound 7 in the form of a pale yellow powder (yield 70%) (1H NMR (400 MHz, CDCl3) 8.69(1H), 8.12 (2H), 8.07-8.02(5H), 7.99-7.95(4H), 7.89-7.84(2H), 7.79-7.75(3H), 7.71-7.65(4H), 7.64-7.54(8H), 7.33(2H), 7.02(1H)).

SYNTHESIS EXAMPLE 4

Synthesis of Compound 3

Compound 3 was synthesized through Reaction Scheme 4 below:

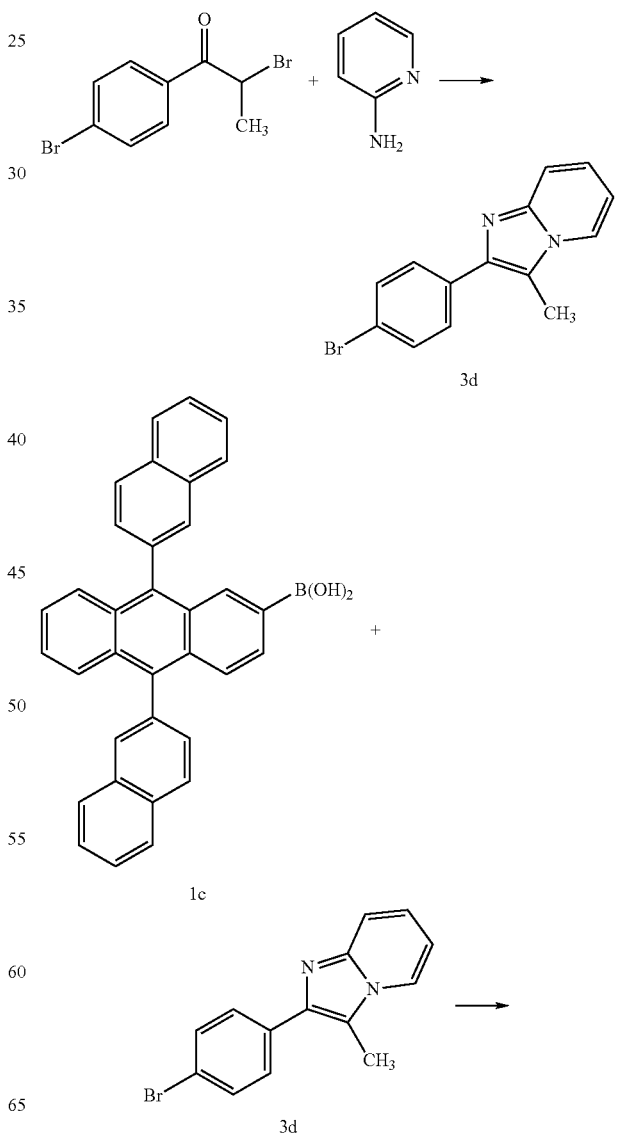

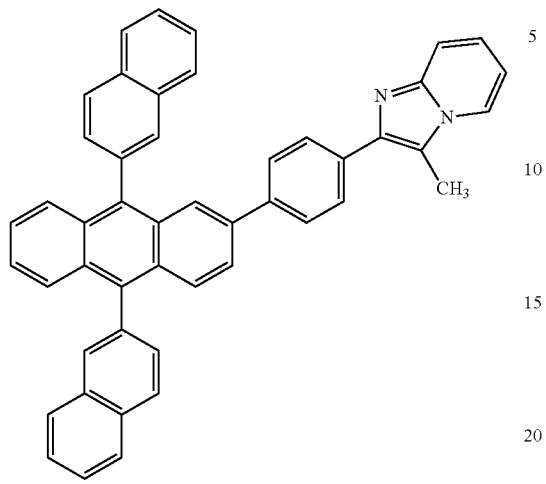

Compound 3

Compound 3 was prepared in the same manner as in Synthesis Example 1, except that Intermediate 3d was used instead of Intermediate 1d. Intermediate 3d was obtained using 2,4'-dibromopropiophenone instead of 2,4'-dibromoacetophenone. 5 g of Intermediate 1c (10.54 mmol) and 2.75 g of Intermediate 3d (9.58 mmol) were subjected to a Suzuki reaction, yielding 4.15 g of Compound 3 in the form of a pale yellow powder (yield 68%). (1H NMR (400 MHz, CDCl$_3$) 8.12(2H), 8.07-8.02(5H), 7.97-7.95(2H), 7.89-7.84(2H), 7.80-7.71(4H), 7.70-7.66(3H), 7.63-7.60(7H), 7.32(2H), 7.15(1H), 6.83(1H), 2.62(3H)).

SYNTHESIS EXAMPLE 5

Synthesis of Compound 2

Compound 2 was synthesized through Reaction Scheme 5 below:

Reaction Scheme 5

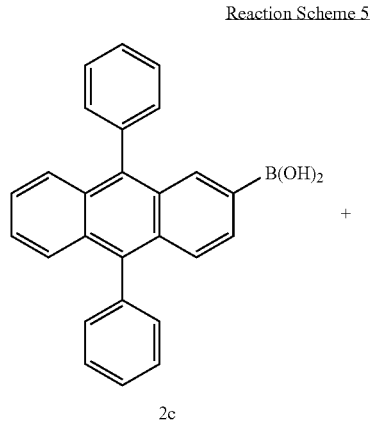

2c

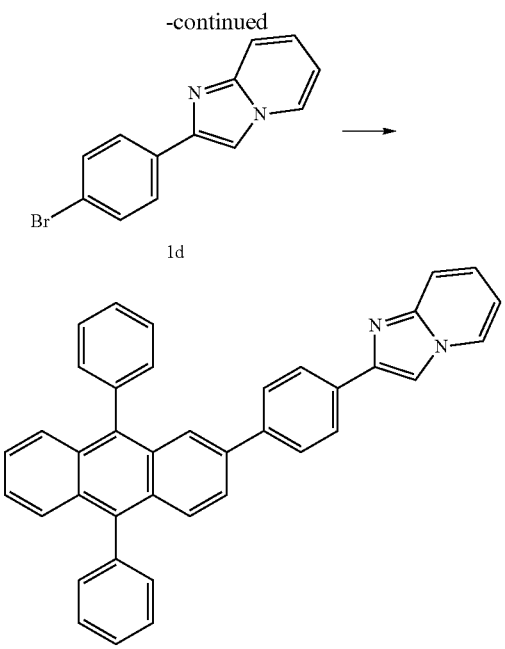

Compound 2

Compound 2 was prepared in the same manner as in Synthesis Example 1, except that Intermediate 2c was used instead of Intermediates 1b and 1c. Intermediate 2c was obtained using phenylmagnesiumbromide instead of 2-naphthylmagnesiumbromide. 5 g of Intermediate 2c (13.36 mmol) and 3.32 g of Intermediate 1d (12.15 mmol) were subjected to a Suzuki reaction, yielding 4.64 g of Compound 2 in the form of pale yellow powder (yield 73%). (1H NMR (400 MHz, CDCl$_3$) 8.11(1H), 7.99(2H), 7.95(1H), 7.86(1H), 7.64(1H), 7.73-7.70(2H), 7.69(1H), 7.66-7.61(7H), 7.58(2H), 7.56-7.50(4H), 7.34(2H), 7.17(1H), 6.78(1H)).

SYNTHESIS EXAMPLE 6

Synthesis of Compound 11

Compound 11 was synthesized through Reaction Scheme 6 below:

Reaction Scheme 6

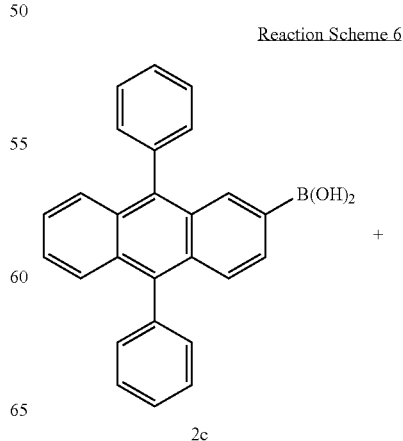

2c

-continued

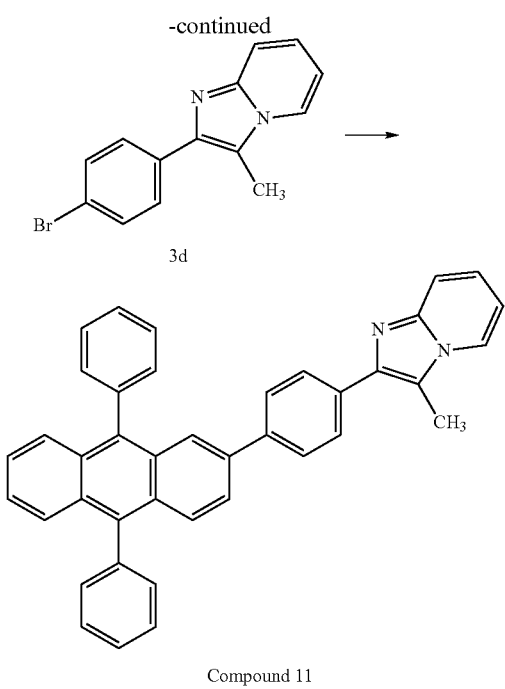

Compound 11

Compound 11 was prepared in the same manner as in Synthesis Examples 5 and 4 using Intermediates 2c and 3d. 5 g of Intermediate 2c (13.36 mmol) and 3.49 g of Intermediate 3d (12.15 mmol) were subjected to a Suzuki reaction, yielding 4.72 g of Compound 11 in the form of pale yellow powder (yield 72%). (1H NMR (400 MHz, CDCl$_3$) 7.97(1H), 7.91 (1H), 7.85(2H), 7.80(1H), 7.73-7.70(2H), 7.69(1H), 7.66-7.61(7H), 7.58(2H), 7.56-7.50(4H), 7.34(2H), 7.19(1H), 6.86(1H), 2.67(3H)).

EXAMPLE 1

A 15 Ω/cm$^2$ (1200 Å), ITO glass substrate was cut to a size of 50 mm×50 mm×0.7 mm, ultrasonically washed with isopropyl alcohol for five minutes and with pure water for 5 minutes. The substrate was then washed with UV ozone for 30 minutes. m-MTDATA was vacuum deposited on the substrate to form a hole injection layer with a thickness of 750 Å. α-NPD was then vacuum deposited on the hole injection layer to form a hole transport layer with a thickness of 150 Å. An emissive layer with a thickness of 300 Å was formed on the hole transport layer using 97 wt % of DSA as a host, and 3 wt % of TBPe as a dopant. Compound 1 prepared by Synthesis Example 1 was vacuum deposited on the emissive layer to form an electron transport layer with a thickness of 200 Å. LiF was vacuum deposited on the electron transport layer to form an electron injection layer with a thickness of 80 Å, and then Al was vacuum deposited on the electron injection layer to form a cathode with a thickness of 3000 Å to complete an organic light emitting diode.

EXAMPLE 2

An organic light emitting diode was manufactured as in Example 1, except that Compound 4 prepared in Synthesis Example 2 was used as the material of the electron transport layer.

EXAMPLE 3

An organic light emitting diode was manufactured as in Example 1, except that Compound 7 prepared in Synthesis Example 3 was used as the material of the electron transport layer.

EXAMPLE 4

An organic light emitting diode was manufactured as in Example 1, except that Compound 3 prepared in Synthesis Example 4 was used as the material of the electron transport layer.

EXAMPLE 5

An organic light emitting diode was manufactured as in Example 1, except that Compound 2 prepared in Synthesis Example 5 was used as the material of the electron transport layer.

EXAMPLE 6

An organic light emitting diode was manufactured as in Example 1, except that Compound 11 prepared in Synthesis Example 6 was used as the material of the electron transport layer.

COMPARATIVE EXAMPLE

An organic light emitting diode was manufactured as in Example 1, except that Alq$_3$ (8-hydroxyquinoline aluminum complex) was used as the material of the electron transport layer.

EVALUATION EXAMPLE

Figure 2:
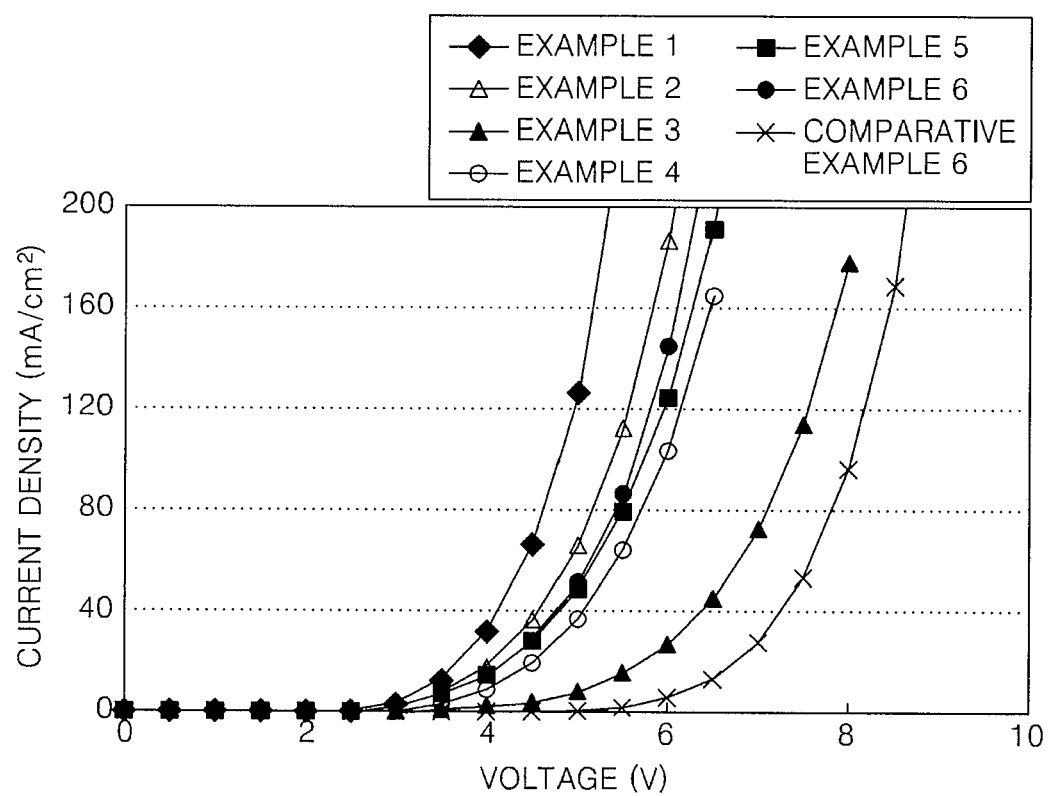
FIG. 2 is a graph comparing voltage-current density properties of the organic light emitting diodes prepared according to Examples 2 through 6 and the organic light emitting diode prepared according to the Comparative Example.

Current density (mA/cm$^2$), driving voltage (V), luminance (cd/m$^2$) and efficiency (lm/W) of each of the organic light emitting diodes prepared according to Examples 1 through 3 and the Comparative Example were measured using a PR650 (Spectroscan) Source Measurement Unit (PhotoResearch Ltd). The results are shown in Table 1 below and in FIGS. 2 and 3. In particular, FIG. 2 is a graph comparing the voltage-current density properties of the organic light emitting diode of Examples 1 through 6 and the organic light emitting diode of the Comparative Example. FIG. 2 is a graph comparing the luminance-efficiency properties of the organic light emitting diode of Examples 1 through 6 and the organic light emitting diode of the Comparative Example.

TABLE 1

| | Electron Transport Layer forming material | Current Density (mA/cm$^2$) | Driving Voltage (V) | Luminance (cd/m$^2$) | Efficiency (lm/W) |
|---|---|---|---|---|---|
| Example 1 | Compound 1 | 10 | 3.4 | 780 | 7.25 |
| Example 2 | Compound 4 | 10 | 3.6 | 774 | 6.67 |
| Example 3 | Compound 7 | 10 | 5.1 | 996 | 6.06 |
| Example 4 | Compound 3 | 10 | 4.0 | 1049 | 8.12 |
| Example 5 | Compound 2 | 10 | 3.7 | 868 | 7.38 |
| Example 6 | Compound 11 | 10 | 3.8 | 905 | 7.54 |
| Comparative Example | Alq$_3$ | 10 | 5.9 | 581 | 2.9 |

Figure 3:
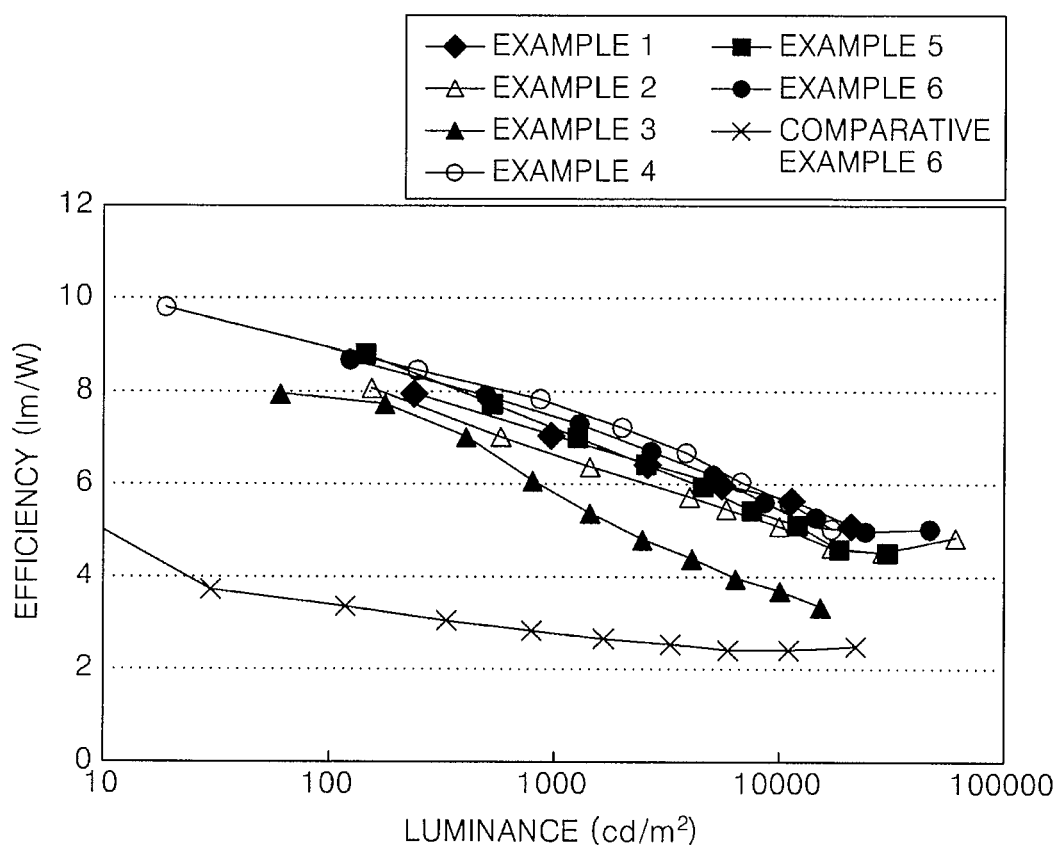
FIG. 3 is a graph comparing luminance-efficiency properties of the organic light emitting diodes prepared according to Examples 2 through 6 and the organic light emitting diode prepared according to the Comparative Example.

As shown in Table 1 and FIGS. 2 and 3, the organic light emitting diodes of Examples 1 through 6 have improved current density, driving voltage, luminance and efficiency compared to the organic light emitting diode of the Comparative Example. Therefore, it can be seen that an organic light emitting diode including an organic layer formed of an imidazopyridine-based compound represented by Formula 1 has higher luminance, higher efficiency, lower driving voltage and a longer life-time than a conventional organic light emitting diode.

The imidazopyridine-based compounds represented by Formula 1 have high electron transporting abilities, and organic light emitting diodes including organic layers having the imidazopyridine-based compounds represented by Formula 1 have low driving voltages, high luminance, high efficiencies and long life-times.

While the present invention has been illustrated and described with reference to certain exemplary embodiments, it will be understood by those of ordinary skill in the art that various changes and modifications may be made to the described embodiments without departing from the spirit and scope of the present invention as defined by the following claims.

What is claimed is:

1. A compound comprising an imidazopyridine-based compound represented by Formula 1:

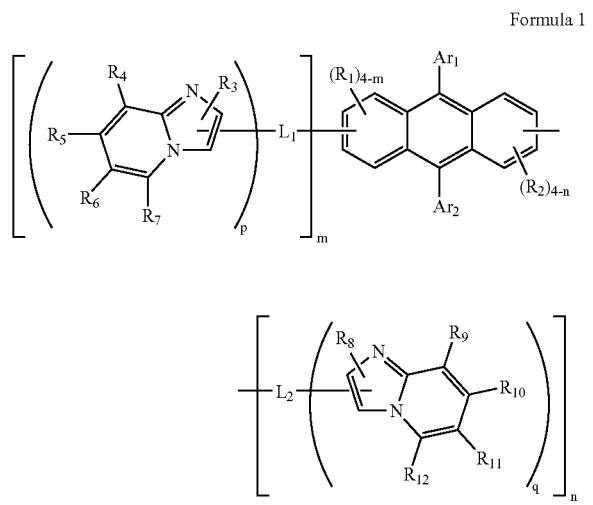

Formula 1 wherein:
each of $R_1$, $R_2$, $R_3$, $R_4$, $R_5$, $R_6$, $R_7$, $R_8$, $R_9$, $R_{10}$, $R_{11}$ and $R_{12}$ is independently selected from the group consisting of hydrogen atoms, halogen atoms, hydroxyl groups, cyano groups, substituted and unsubstituted $C_1$-$C_{30}$ alkyl groups, substituted and unsubstituted $C_1$-$C_{30}$ alkoxy groups, substituted and unsubstituted $C_1$-$C_{30}$ acyl groups, substituted and unsubstituted $C_2$-$C_{30}$ alkenyl groups, substituted and unsubstituted $C_2$-$C_{30}$ alkynyl groups, substituted and unsubstituted $C_6$-$C_{30}$ aryl groups, and substituted and unsubstituted $C_3$-$C_{30}$ heteroaryl groups;
at least two of $R_4$, $R_5$, $R_6$ and $R_7$ form a saturated or unsaturated ring;
at least two of $R_9$, $R_{10}$, $R_{11}$ and $R_{12}$ form a saturated or unsaturated ring;
each of $L_1$ and $L_2$ is independently selected from the group consisting of single bonds, substituted and unsubstituted $C_1$-$C_{30}$ alkylene groups, substituted and unsubstituted $C_6$-$C_{30}$ arylene groups, and substituted and unsubstituted $C_3$-$C_{30}$ heteroarylene groups;
each of $Ar_1$ and $Ar_2$ is independently selected from the group consisting of substituted and unsubstituted $C_6$-$C_{30}$ aryl groups, and substituted and unsubstituted $C_3$-$C_{30}$ heteroaryl groups;
each of p and q is independently an integer ranging from 1 to 5; and
each of m and n is independently an integer ranging from 0 to 4, wherein both m and n are not 0.

2. The compound of claim 1, wherein each of $R_1$ through $R_{12}$ is independently selected from the group consisting of hydrogen atoms, substituted and unsubstituted $C_1$-$C_{10}$ alkyl groups, substituted and unsubstituted $C_2$-$C_{10}$ alkenyl groups, substituted and unsubstituted $C_6$-$C_{12}$ aryl groups, and substituted and unsubstituted $C_3$-$C_{12}$ heteroaryl groups.

3. The compound of claim 1, wherein each of $R_1$ through $R_{12}$ is independently selected from hydrogen atoms, $C_1$-$C_{10}$ alkyl groups, $C_1$-$C_{10}$ haloalkyl groups, $C_2$-$C_{10}$ alkenyl groups, $C_2$-$C_{10}$ haloalkenyl groups, phenyl groups, halophenyl groups, $C_1$-$C_{10}$ alkylphenyl groups, $C_1$-$C_{10}$ alkoxyphenyl groups, naphthyl groups, halonaphthyl groups, $C_1$-$C_{10}$ alkylnaphthyl groups, and $C_1$-$C_{10}$ alkoxynaphthyl groups.

4. The compound of claim 1, wherein at least two of $R_4$ through $R_7$ form a substituted or unsubstituted $C_6$-$C_{12}$ aromatic ring.

5. The compound of claim 1, wherein at least two of $R_9$ through $R_{12}$ form a substituted or unsubstituted $C_6$-$C_{12}$ aromatic ring.

6. The compound of claim 1, wherein each of $L_1$ and $L_2$ is independently selected from the group consisting of substituted and unsubstituted $C_6$-$C_{12}$ arylene groups, and substituted and unsubstituted $C_3$-$C_{12}$ heteroarylene groups.

7. The compound of claim 1, wherein each of $L_1$ and $L_2$ is independently selected from the group consisting of phenylene groups, halophenylene groups, $C_1$-$C_{10}$ alkylphenylene groups, $C_1$-$C_{10}$ alkoxyphenylene groups, naphthylene groups, halonaphthylene groups, $C_1$-$C_{10}$ alkylnaphthylene groups, and $C_1$-$C_{10}$ alkoxynaphthylene groups.

8. The compound of claim 1, wherein each of $Ar_1$ and $Ar_2$ is independently selected from the group consisting of substituted and unsubstituted $C_6$-$C_{12}$ aryl groups, and substituted and unsubstituted $C_3$-$C_{12}$ heteroaryl groups.

9. The compound of claim 1, wherein each of $Ar_1$ and $Ar_2$ is independently selected from the group consisting of phenyl groups, halophenyl groups, $C_1$-$C_{10}$ alkylphenyl groups, $C_1$-$C_{10}$ alkoxyphenyl groups, naphthyl groups, halonaphthyl groups, $C_1$-$C_{10}$ alkylnaphthyl groups, $C_1$-$C_{10}$ alkoxynaphthyl groups, pyridinyl groups, halopyridinyl groups, $C_1$-$C_{10}$ alkylpyridinyl groups, $C_1$-$C_{10}$ alkoxypyridinyl groups, quinolinyl groups, haloquinolinyl groups, $C_1$-$C_{10}$ alkylquinolinyl groups, $C_1$-$C_{10}$ alkoxyquinolinyl groups, isoquinolinyl groups, haloisoquinolinyl groups, $C_1$-$C_{10}$ alkylisoquinolinyl groups, and $C_1$-$C_{10}$ alkoxyisoquinolinyl groups.

10. The compound of claim 1, wherein m is 0, and n is 1.

11. The compound of claim 1, wherein both m and n are 1.

12. The imidazopyridine-based compound of claim 1, wherein the imidazopyridine based compound is selected from the group consisting of compounds represented by Formulae 1a, 1b, 1c and 1d:

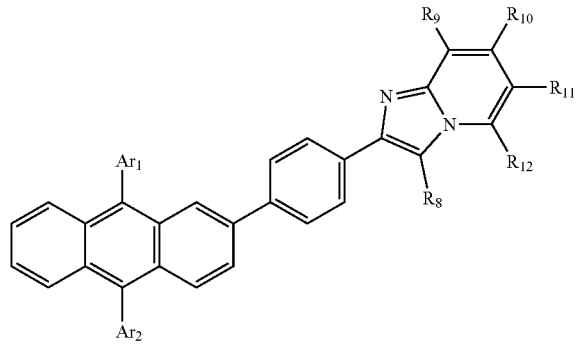
Formula 1a
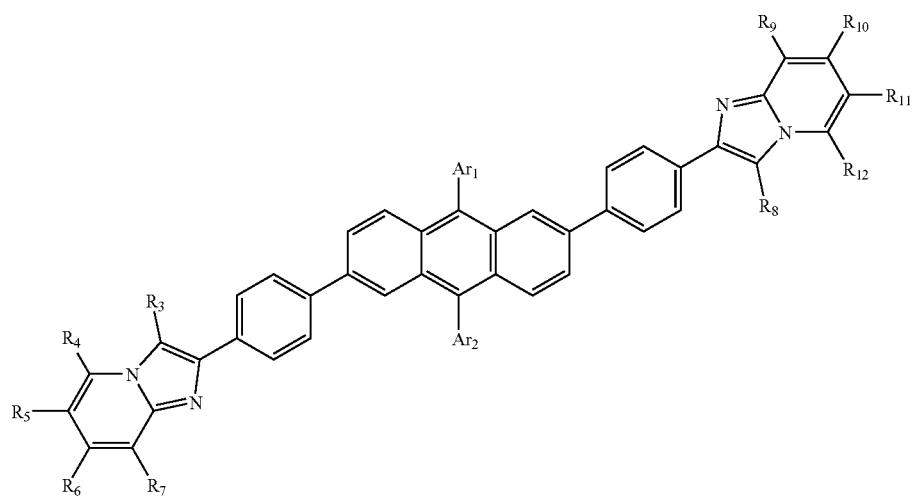
Formula 1b
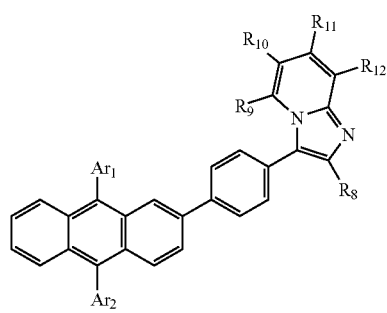
Formula 1c
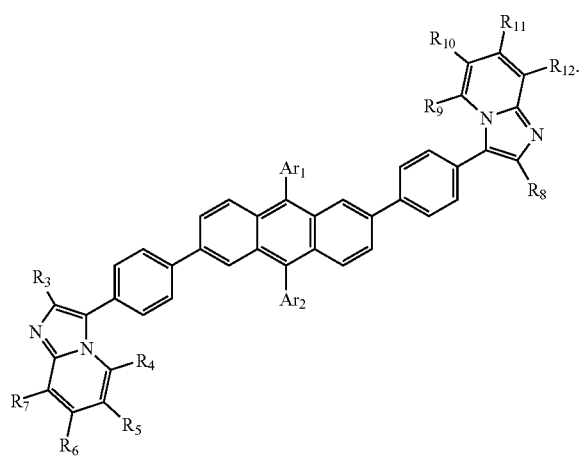
Formula 1d
13. The compound of claim 1, wherein the imidazopyridine-based compound is selected from the group consisting of Compounds 1 through 11:

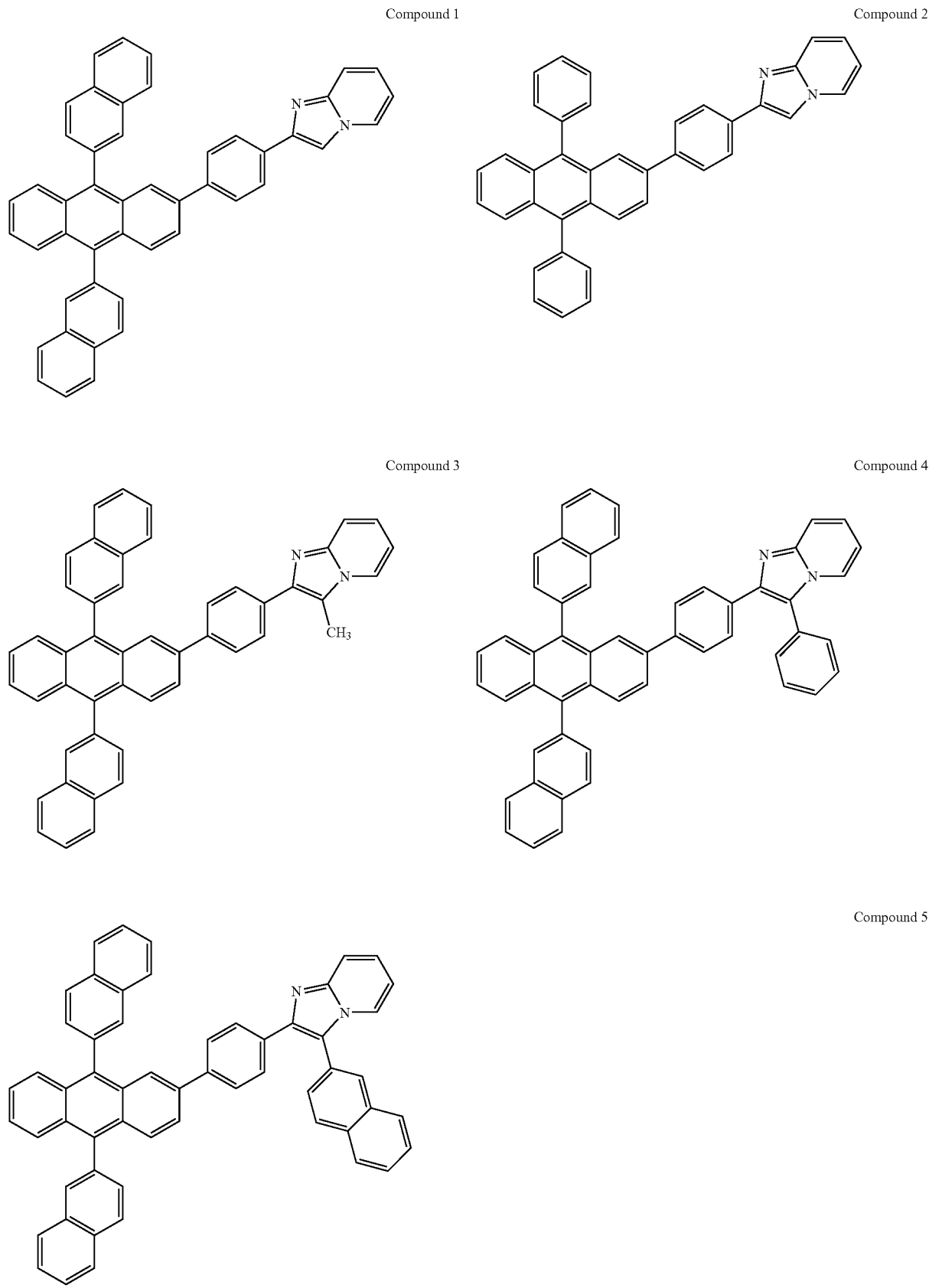

-continued
Compound 6
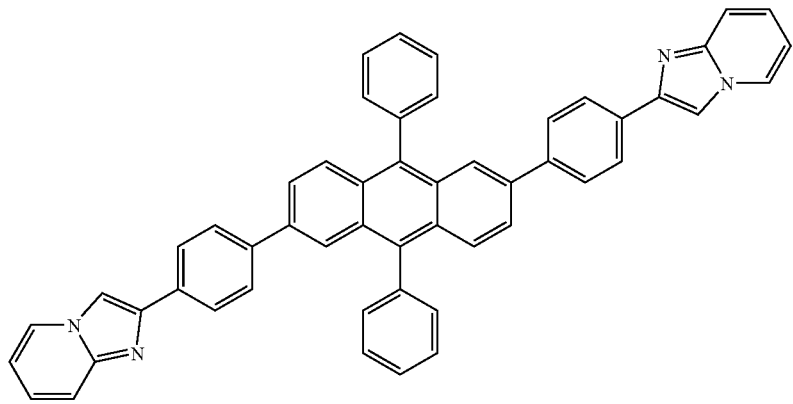
Compound 7
Compound 8
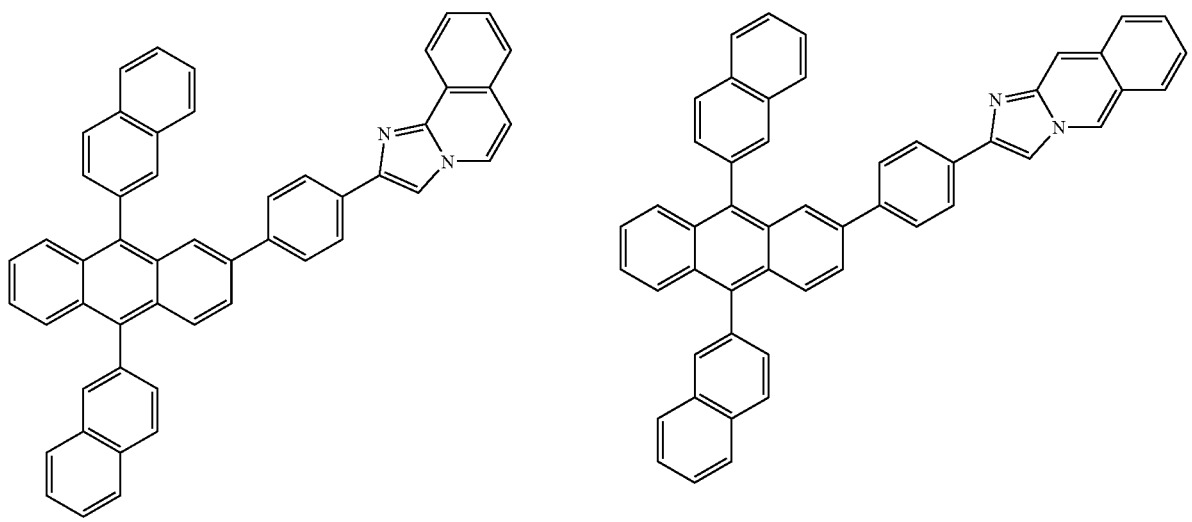
Compound 9
Compound 10
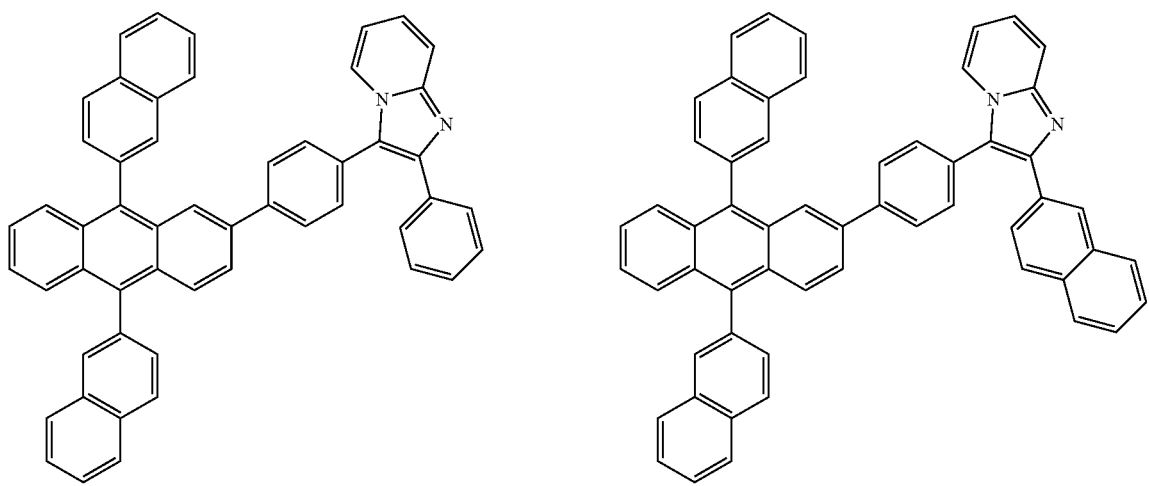

-continued
Compound 11
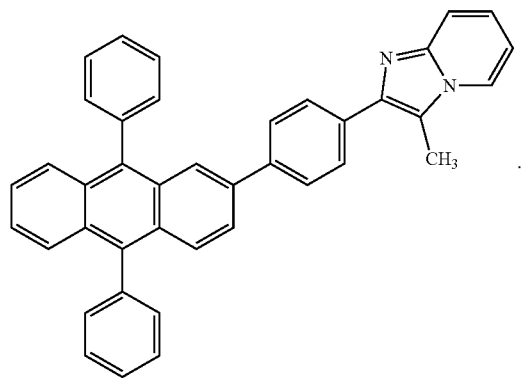
* * * * *